(12) United States Patent
Moore et al.

(10) Patent No.: US 9,907,968 B2
(45) Date of Patent: Mar. 6, 2018

(54) TEMPORARY ELECTRODE CONNECTION FOR WIRELESS PACING SYSTEMS

(71) Applicant: EBR Systems, Inc., Sunnyvale, CA (US)

(72) Inventors: David F. Moore, San Carlos, CA (US); Mark W. Cowan, San Jose, CA (US); N. Parker Willis, Atherton, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 15/043,210

(22) Filed: Feb. 12, 2016

(65) Prior Publication Data
US 2016/0158560 A1 Jun. 9, 2016

Related U.S. Application Data

(60) Division of application No. 12/890,308, filed on Sep. 24, 2010, now Pat. No. 9,283,392, which is a
(Continued)

(51) Int. Cl.
*A61N 1/378* (2006.01)
*A61B 5/042* (2006.01)
(Continued)

(52) U.S. Cl.
CPC ............ *A61N 1/3787* (2013.01); *A61B 5/042* (2013.01); *A61N 1/362* (2013.01); *A61N 1/3702* (2013.01);
(Continued)

(58) Field of Classification Search
CPC .. A61N 1/37205; A61N 1/362; A61N 1/3756; A61N 1/3787; A61N 1/37223
(Continued)

(56) References Cited

U.S. PATENT DOCUMENTS 3,057,356 A 10/1962 Greatbatch
3,659,615 A 5/1972 Enger
(Continued)

FOREIGN PATENT DOCUMENTS

DE 4330680 A1 3/1995
WO WO-9725098 A1 7/1997
(Continued)

OTHER PUBLICATIONS

Abraham et al. For the MIRACLE study group, Cardiac Resynchronization in Chronic Heart Failure. N Engl J Med 346:1845-53 (2002).
(Continued)

*Primary Examiner* — Alyssa M Alter
(74) *Attorney, Agent, or Firm* — Wilson Sonsini Goodrich & Rosati

(57) ABSTRACT

Delivery of an implantable wireless receiver-stimulator (R-S) into the heart using delivery catheter is described. R-S comprises a cathode and an anode and wirelessly receives and converts energy, such as acoustic ultrasound energy, to electrical energy to stimulate the heart. Conductive wires routed through the delivery system temporarily connect R-S electrodes to external monitor and pacing controller. R-S comprises a first temporary electrical connection from the catheter to the cathode, and a second temporary electrical connection from the catheter to the anode. Temporary electrical connections allow external monitoring of heart's electrical activity as sensed by R-S electrodes to determine tissue viability for excitation as well as to assess energy conversion efficiency.

25 Claims, 21 Drawing Sheets

Related U.S. Application Data continuation of application No. PCT/US2009/037978, filed on Mar. 23, 2009.

(60) Provisional application No. 61/039,335, filed on Mar. 25, 2008.

(51) Int. Cl.
*A61N 1/362* (2006.01)
*A61N 1/372* (2006.01)
*A61N 1/375* (2006.01)
*A61N 1/37* (2006.01)
*A61B 17/34* (2006.01)

(52) U.S. Cl.
CPC ....... *A61N 1/3756* (2013.01); *A61N 1/37205* (2013.01); *A61B 17/3468* (2013.01); *A61N 1/37223* (2013.01)

(58) Field of Classification Search
USPC .......................................................... 607/9
See application file for complete search history.

(56) References Cited

U.S. PATENT DOCUMENTS

| | | |
|---|---|---|
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,835,865 A | 9/1974 | Bowers |
| 3,857,382 A | 12/1974 | Williams et al. |
| 3,893,461 A | 7/1975 | Preston |
| 3,939,844 A | 2/1976 | Pequignot |
| 3,942,534 A | 3/1976 | Allen et al. |
| 4,181,133 A | 1/1980 | Kolenik et al. |
| 4,256,115 A | 3/1981 | Bilitch |
| 4,265,228 A | 5/1981 | Zoll |
| 4,280,502 A | 7/1981 | Baker, Jr. et al. |
| 4,343,312 A | 8/1982 | Cals et al. |
| 4,373,531 A | 2/1983 | Wittkampf et al. |
| 4,399,818 A | 8/1983 | Money |
| 4,498,478 A | 2/1985 | Bourgeois |
| 4,561,442 A | 12/1985 | Vollmann et al. |
| 4,577,633 A | 3/1986 | Berkovits et al. |
| 4,651,716 A | 3/1987 | Forester et al. |
| 4,651,740 A * | 3/1987 | Schroeppel ........ A61N 1/37217 181/139 |
| 4,690,144 A | 9/1987 | Rise et al. |
| 4,830,006 A | 5/1989 | Haluska et al. |
| 5,018,523 A | 5/1991 | Bach, Jr. et al. |
| 5,063,928 A | 11/1991 | Grevis et al. |
| 5,103,129 A | 4/1992 | Slayton et al. |
| 5,113,859 A | 5/1992 | Funke |
| 5,165,403 A | 11/1992 | Mehra |
| 5,170,784 A | 12/1992 | Ramon et al. |
| 5,174,289 A | 12/1992 | Cohen |
| 5,193,539 A | 3/1993 | Schulman et al. |
| 5,292,338 A | 3/1994 | Bardy |
| 5,377,166 A | 12/1994 | Kuhn |
| 5,405,367 A | 4/1995 | Schulman et al. |
| 5,411,535 A | 5/1995 | Fujii et al. |
| 5,433,731 A | 7/1995 | Hoegnelid et al. |
| 5,557,210 A * | 9/1996 | Cappa .................... A61N 1/05 324/538 |
| 5,674,251 A | 10/1997 | Combs et al. |
| 5,749,909 A | 5/1998 | Schroeppel et al. |
| 5,751,539 A | 5/1998 | Stevenson et al. |
| 5,757,104 A | 5/1998 | Getman et al. |
| 5,766,227 A | 6/1998 | Nappholz et al. |
| 5,782,880 A | 7/1998 | Lahtinen et al. |
| 5,800,464 A | 9/1998 | Kieval |
| 5,814,089 A | 9/1998 | Stokes et al. |
| 5,817,130 A | 10/1998 | Cox et al. |
| 5,843,136 A | 12/1998 | Zhu et al. |
| 5,844,349 A | 12/1998 | Oakley et al. |
| 5,871,506 A | 2/1999 | Mower |
| 5,935,158 A | 8/1999 | Holmstrom et al. |
| 5,978,204 A | 11/1999 | Stevenson |
| 5,998,910 A | 12/1999 | Park et al. |
| 6,037,704 A | 3/2000 | Welle |
| 6,070,101 A | 5/2000 | Struble et al. |
| 6,078,837 A | 6/2000 | Peterson et al. |
| 6,110,098 A | 8/2000 | Renirie et al. |
| 6,141,588 A | 10/2000 | Cox et al. |
| 6,208,894 B1 | 3/2001 | Schulman et al. |
| 6,223,079 B1 | 4/2001 | Bakels et al. |
| 6,233,484 B1 | 5/2001 | Ben-Haim et al. |
| 6,236,887 B1 | 5/2001 | Ben-Haim et al. |
| 6,264,611 B1 | 7/2001 | Ishikawa et al. |
| 6,285,906 B1 | 9/2001 | Ben-Haim et al. |
| 6,298,268 B1 | 10/2001 | Ben-Haim et al. |
| 6,317,631 B1 | 11/2001 | Ben-Haim et al. |
| 6,330,475 B1 | 12/2001 | Renirie et al. |
| 6,330,476 B1 | 12/2001 | Ben-Haim et al. |
| 6,363,279 B1 | 3/2002 | Ben-Haim et al. |
| 6,366,816 B1 | 4/2002 | Marchesi |
| 6,408,205 B1 | 6/2002 | Renirie et al. |
| 6,424,234 B1 | 7/2002 | Stevenson |
| 6,425,869 B1 | 7/2002 | Rafter et al. |
| 6,428,484 B1 | 8/2002 | Battmer et al. |
| 6,439,236 B1 | 8/2002 | Porter et al. |
| 6,442,424 B1 | 8/2002 | Ben-Haim et al. |
| 6,445,953 B1 | 9/2002 | Bulkes et al. |
| 6,463,324 B1 | 10/2002 | Ben-Haim et al. |
| 6,522,926 B1 | 2/2003 | Kieval et al. |
| 6,527,729 B1 | 3/2003 | Turcott |
| 6,534,895 B2 | 3/2003 | Kadota et al. |
| RE38,119 E | 5/2003 | Mower |
| 6,584,358 B2 | 6/2003 | Carter et al. |
| 6,600,955 B1 | 7/2003 | Zierhofer |
| 6,628,989 B1 | 9/2003 | Penner et al. |
| 6,645,145 B1 | 11/2003 | Dreschel et al. |
| 6,647,292 B1 | 11/2003 | Bardy et al. |
| 6,654,638 B1 | 11/2003 | Sweeney |
| 6,671,547 B2 | 12/2003 | Lyster et al. |
| 6,687,538 B1 | 2/2004 | Hrdlicka et al. |
| 6,707,230 B2 | 3/2004 | Smith et al. |
| 6,721,597 B1 | 4/2004 | Bardy et al. |
| 6,725,093 B1 | 4/2004 | Ben-Haim et al. |
| 6,728,576 B2 | 4/2004 | Thompson et al. |
| 6,754,528 B2 | 6/2004 | Bardy et al. |
| 6,754,531 B1 | 6/2004 | Kroll et al. |
| 6,764,446 B2 | 7/2004 | Wolinsky et al. |
| 6,788,974 B2 | 9/2004 | Bardy et al. |
| 6,795,732 B2 | 9/2004 | Stadler et al. |
| 6,798,716 B1 | 9/2004 | Charych |
| 6,834,204 B2 | 12/2004 | Ostroff et al. |
| 6,856,835 B2 | 2/2005 | Bardy et al. |
| 6,970,742 B2 | 11/2005 | Mann et al. |
| 6,983,185 B2 | 1/2006 | Ley et al. |
| 7,010,350 B2 | 3/2006 | Kralik |
| 7,024,248 B2 | 4/2006 | Penner et al. |
| 7,043,292 B2 | 5/2006 | Tarjan et al. |
| 7,160,258 B2 | 1/2007 | Imran et al. |
| 7,198,603 B2 | 4/2007 | Penner et al. |
| 7,200,437 B1 | 4/2007 | Nabutovsky et al. |
| 7,283,874 B2 | 10/2007 | Penner |
| 7,349,740 B2 | 3/2008 | Soykan et al. |
| 7,489,967 B2 | 2/2009 | Von Arx et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,702,392 B2 | 4/2010 | Echt et al. |
| 7,765,001 B2 | 7/2010 | Echt et al. |
| 9,283,392 B2 | 3/2016 | Moore et al. |
| 2002/0077673 A1 | 6/2002 | Penner et al. |
| 2003/0013974 A1 | 1/2003 | Natarajan et al. |
| 2004/0015104 A1 | 1/2004 | Goldberger |
| 2004/0064166 A1 | 4/2004 | Thompson et al. |
| 2004/0106959 A1 | 6/2004 | Schmidt et al. |
| 2004/0162501 A1 | 8/2004 | Imran |
| 2004/0167580 A1 | 8/2004 | Mann et al. |

(56) References Cited

U.S. PATENT DOCUMENTS

| | | |
|---|---|---|
| 2004/0204744 A1 | 10/2004 | Penner et al. |
| 2004/0243192 A1 | 12/2004 | Hepp et al. |
| 2004/0260214 A1 | 12/2004 | Echt et al. |
| 2004/0260346 A1 | 12/2004 | Overall et al. |
| 2005/0065426 A1 | 3/2005 | Porat et al. |
| 2005/0070962 A1 | 3/2005 | Echt et al. |
| 2006/0009831 A1 | 1/2006 | Lau et al. |
| 2006/0106442 A1 | 5/2006 | Richardson et al. |
| 2006/0135999 A1 | 6/2006 | Bodner et al. |
| 2006/0136004 A1 | 6/2006 | Cowan et al. |
| 2006/0136005 A1 | 6/2006 | Brisken et al. |
| 2006/0224067 A1 | 10/2006 | Giftakis et al. |
| 2006/0241701 A1 | 10/2006 | Markowitz et al. |
| 2007/0027508 A1 | 2/2007 | Cowan |
| 2007/0032749 A1 | 2/2007 | Overall et al. |
| 2007/0067000 A1 | 3/2007 | Strother et al. |
| 2007/0088394 A1 | 4/2007 | Jacobson |
| 2007/0088397 A1 | 4/2007 | Jacobson |
| 2007/0088398 A1 | 4/2007 | Jacobson |
| 2007/0150009 A1 | 6/2007 | Kveen et al. |
| 2007/0232936 A1 | 10/2007 | Mann et al. |
| 2007/0260286 A1 | 11/2007 | Giftakis et al. |
| 2007/0265677 A1 | 11/2007 | Giftakis et al. |
| 2008/0294208 A1 | 11/2008 | Willis et al. |

FOREIGN PATENT DOCUMENTS

| | | |
|---|---|---|
| WO | WO-9961058 A1 | 12/1999 |
| WO | WO-0176687 A2 | 10/2001 |
| WO | WO-03070323 A1 | 8/2003 |

OTHER PUBLICATIONS

ACC/AHA Task Force on Practice Guidelines, Evaluation and Management of Chronic Heart Failure in the Adult. JACC 38:2101-13 (2002).

Allessie et al. Regional Control of Atrial Fibrillation by Rapid Pacing in Conscious Dogs. Circulation 84:1689-97 (1991).

Ansalone et al. Bi-ventricular Pacing | Heart Failure:Back to Basics in the Pathophysiology of Left Bundle Branch Block to Reduce the Number of Nonresponders. Am J Cardiol 91:55F-61F (2003).

Auricchio et al. Cardiac Resynchronization Therapy: Current State of the Art. Circulation 109:300-307 (2004).

Bardy, et al. The Totally Subcutaneous ICD System (The S-ICD). PACE. 24:578 (2002).

Becker et al, Suppression of Atrial Fibrillation by Multisite and Septal Pacing in a Novel Experimental Model. Cardiovascular Research 54(2):476-481 (2001).

Bradley, et al. Cardiac resynchronization and death from progressive heart failure: a meta-analysis of randomized controlled trials. JAMA 289(6):730-40 (2003).

Camm, et al. Chapter 6: Nonpharmaceutical treatment of atrial fibrillation, In Atrial Fibrillation. Facts from Yesterday—Ideas for tomorrow. Futura Publishing Company, Inc., Armonk, NY, pp. 125-147 (1994).

Dalecki, et al. Effects of Pulsed Ultrasound on the Frog Heart: I. Thresholds for Changes in Cardiac Rhythm and Aortic Pressure. Ultrasound in Med. & Biol. 19:385-390 (1993).

Dalecki et al. Effects of Pulsed Ultrasound on the Frog Heart: II. An Investigation of Heating as a Potential Mechanism. Ultrasound in Med. & Biol. 19:391-398 (1993).

Dalecki et al. Thresholds for premature ventricular contractions in frog hearts exposed to lithotripter fields. Ultrasound in Med. & Biol. 17:341-346 (1991).

Daoud, et al. Implantation techniques and chronic lead parameters of biventricular pacing dual-chamber defibrillators. J Cardiovasc Electrophysiol 13(10):964-70 (2002).

Daubert, et al. Permanent left ventricular pacing with transvenous leads inserted into the coronary veins. Pacing Clin Electrophysiol 21(1 Pt 2):239-45 (1998).

Daubert, et al. Use of Specifically Designed Coronary Sinus Leads for Permanent Left Ventricular Pacing: Preliminary Experience. Pace 20:II—NASPE Abstract 17 (1997).

David Trial Investigators, The Dual Chamber and WI Implantable Defibrillator (DAVID) Trial. JAMA 288:3115-3123 (2002).

Deshmukh et al. Direct His-bundle pacing: present and future. PACE 27 [Pt.II]:862-70 (2004).

Ellenbogen et al. Detection and Management of an Implantable Cardioverter Defibrillator Lead Failure. JACC 41:73-80 (2003).

European search report and search opinion dated Oct. 4, 2011 for Application No. 9725046.8.

Feldman et al, Comparison of medical therapy, resynchronization and defibrillation therapies in heart failure trial (COMPANION). Presented at ACC 2003 Late Breaking Clinical Trials, 1 page.

Franz, Mechano-electrical feedback in ventricular myocardium. Cardiovascular Research 32:15-24 (1996).

Gregoratos, et al. ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 106:2145-2161 (2002).

Hu et al. Stretch-Activated Ion Channels in the Hear. J. Mot. Cell Cardiol. 1997; 29:1511-1523.

International search report and written opinion dated May 18, 2009 for PCT/US2009/037978.

Johnson et al. Adaptive Pacing During Ventricular Fibrillation. Pace 26:1824-36 (2003).

Kalman J.M. et al, Regional Entrainment of Atrial Fibrillation in Man. J Cardiovasc Electrophysiol 7:867-76 (1991).

Kass et al. Improved Left Ventricular Mechanics from Acute VDD Pacing in Patients with Dilated Cardiomyopathy and Ventricular Conduction Delay. Circulation 99:1567-73 (1999).

Kenknight, et al. Regional Capture of Fibrillating Ventricular Myocardium. Circ Res 77:849-55. Retrieve from the Internet: circres.ahajournals.org/cgi/content/full/77/4/849 (1999).

Kohl et al. Stretch-Induced Changes in Heart Rate and Rhythm: Clinical Observations, Experiments and Mathematical Models. Progress in Biophysics & Molecular Biology 71:91-138 (1999).

Kohl et al. Sudden Cardiac Death by Commotio Cordis: Role of Mechano-Electrical Feedback. Cardiovascular Research 50:280-289 (2001).

Leclercq, et al. Is Dual Site Better than Single Site Atrial Pacing in the Prevention of Atrial Fibrillation? PACE 23:2102-7 (2000).

Leclercq et al. Systolic Improvement and Mechanical Resynchronization does not Require Electrical Synchrony in the Dilated Failing Heart with Left Bundle-Branch Block. Circulation 106:1760-1763 (2002).

Leclerq, et al. Acute Hemodynamic Effects of Biventricular DDD Pacing in Patients with End-Stage Heart Failure. JACC 32:1825-1831 (1998).

Lee et al. Effect of implantable Defibrillators of Arrhythmic Events and Mortality in the Multicenter Unsustained Tachycardia Trial. Circulation. 106:233-238 (2002).

Linde et al. Long-Term Benefits of Biventricular Pacing in Congestive Heart Failure: From the Multisite Stimulation in Cardiomyopathy (MUSTIC) Study. J Am Coll Cardiol 40:111-118 (2002).

Marrouche, et al. Nonexcitatory stimulus delivery improves left ventricular function in hearts with left bundle branch block. J Carcovasc Electrophysiol. 13(7):691-695 (2002).

McPherson, et al. Seizing the Science of Ultrasound Beyond Imaging and Into Physiology and Therapeutics. Journal of the American College of Cardiology 41:1628-30 (2003).

Meltzer, et al. Therapeutic Cardiac Ultrasound. American Journal of Cardiology 67:422-4 (1991).

Miracle Trial Investigators. Combined Cardiac Resynchronization and Implantable Cardioversion Defibrillation in Advanced Heart Failure: the Miracle ICD Trial. JAMA 289:2685-2694 (2003).

Mirza et al, Biatrial Pacing for Paroxysmal Atrial Fibrillation. J Am Coll Cardiol 40:457-463 (2002).

(56) References Cited

OTHER PUBLICATIONS

Miyamoto, et al. Coronary Vasodilation by Noninvasive Transcutaneous Ultrasound an in ivo Canine Study. Journal of the American College of Cardiology 41:1623-7 (2003).
Mohri, et al. Cardiac Contractility Modulation by electric Currents Applied During the Refractory Period. Am J Physiol Heart Ciro Physiol 282:H1642-1647 (2002).
Mond. Selective Site Pacing: The Future of Cardiac Pacing? PACE 27:835-836 (2004).
Mortimer, et al. Letter to the Editor: Altered Myocardial Contractility with Pulsed Ultrasound. Ultrasound in Med and Biol 13(9):L567-9 (1987).
Moss et al. Prophylactic Implantation of a Defibrillator in Patients with Myocardial Infarction and Reduced Ejection Fraction. N Engl J Med. 346:877-933 (2002).
Niehaus et al. Non-Contact Cardiac Stimulation with locused Ultrasound Pulses. PACE 26:1023 (2003).
Nielsen et al. A Randomized Comparison of Atrial and Dual-Chambered Pacing in 177 Consecutive Patients With Sick Sinus Syndrome. J Am Coll Cardiol 42:614-623 (2003).
Nishida, et al. Extracorporeal cardiac shock wave therapy markedly ameliorates ischemia-induced myocardial dysfunction in pigs in vivo. Circulation 110:3055-3061 (2004).
Nolte, et al. Mechanically Induced Ventricular Extrasystoles in the Isolated Perfused Guinea-Pig Heart. Arzneim.-Forsch/Drug Research. 37(11): 1025-1029 (1987).
Notice of allowance dated Nov. 10, 2015 for U.S. Appl. No. 12/890,308.
Office action dated Feb. 12, 2013 for U.S. Appl. No. 12/890,308.
Office action dated Mar. 23, 2015 for U.S. Appl. No. 12/890,308.
Office action dated May 27, 2014 for U.S. Appl. No. 12/890,308.
Office action dated Jul. 8, 2012 for U.S. Appl. No. 12/890,308.
Pappone, et al. Cardiac Contractility Modulation by electric currents applied during the refractory period in patients with heart failure secondary to ischemic or idiopathic dilated cardiomyopathy. Am J Cardiol 90(12):1307-1313 (2002).
Pappone, et al. First Human Chronic Experience with Cardiac Contractility Modulation by Nonexcitatory Electrical Currents for Treating Systolic Heart Failure: Mid-Term Safety and Efficacy Results from a Multicenter Study. J Cardiovasc Electrophysiol 15:418-427 (2004).
Peschar et al. Left Ventricular Septal and Apex Pacing for Optimal Pump Function in Canine Hearts. J Am Coll Cardiol 41:1218-26 (2003).
Reiter et al.., Effects of Mechano-Electrical Feedback: Potential Arrhythmogenic Influence in Patients With Congestive Heart Failure. Cardiovascular Research 32:44-51 (1996).
Smailys et al. Investigation of the Possibilities of cardiac Defibrillation by Ultrasound. Resuscitation 9:233-242 (1981).
Sowton, Clinical Results with the Tachylog Antitachycardia Pacemaker. PACE 7(Part II):1313-1317 (1984).
Soykan. Automated Piecewise Linear Modeling of Pacing Leads. Engineering in Medicine and Biology Society, Engineering Advances: New Opportunities for Biomedical Engineers. Proceedings of the 16th Annual International Conference of the IEEE 1:53-54 (Nov. 3-6, 1994).
Stix, et al. Chronic electrical stimulation during the absolute refractory period of the myocardium improves severe heart failure. European Heart J 25:650-655 (2004).
Suchkova, et al. Ultrasound improves tissue perfusion in ischemic tissue through a nitric oxide-dependent mechanism. Throm Haemost. 88:865-70 (2002).
Tacker. Chapter 1: Fibrillation causes and criteria for defibrillation. In Defibrillation of the Heart. Tacker, WA, ed. Mosby-Year Book, Inc., St. Louis, Missouri, pp. 1-14 (1994).
The Antiarrhythmics Versus Implantable Defibrillators (AVID) Investigators, A Comparison of Antiarrhythmic Drug Therapy with Implantable Defibrillators in Patients Resuscitated from Near Fatal Ventricular Arrhythmias. N Engl J Med. 337:1576-1583 (1997).
Valls-Bertault et al. Adverse Events with Transvenous Left Ventricular Pacing in Patients with Severe Heart Failure: Early Experience from a Single Centre. Europace 3:60-63 (2001).
Warren et al. Clinical Evaluation of Automatic Tachycardia Diagnosis by an Implanted Device. PACE 9 (Part II):1079-1083 (1986).
Zakharov, et al. The action of Ultrasound on the Contraction Strength and Cation Potential of the Papillary Muscle of the Rat Heart. Biul Eksp Biol Med. 107(4):423-6 (1989).
Zakharov, et al. The Effect of Acoustic Cavitation on the Contraction Force and Membrane Potential of Rat Papillary Muscle. Ultrasound Med. Biol. 15 (6):561-5 (1989).

* cited by examiner

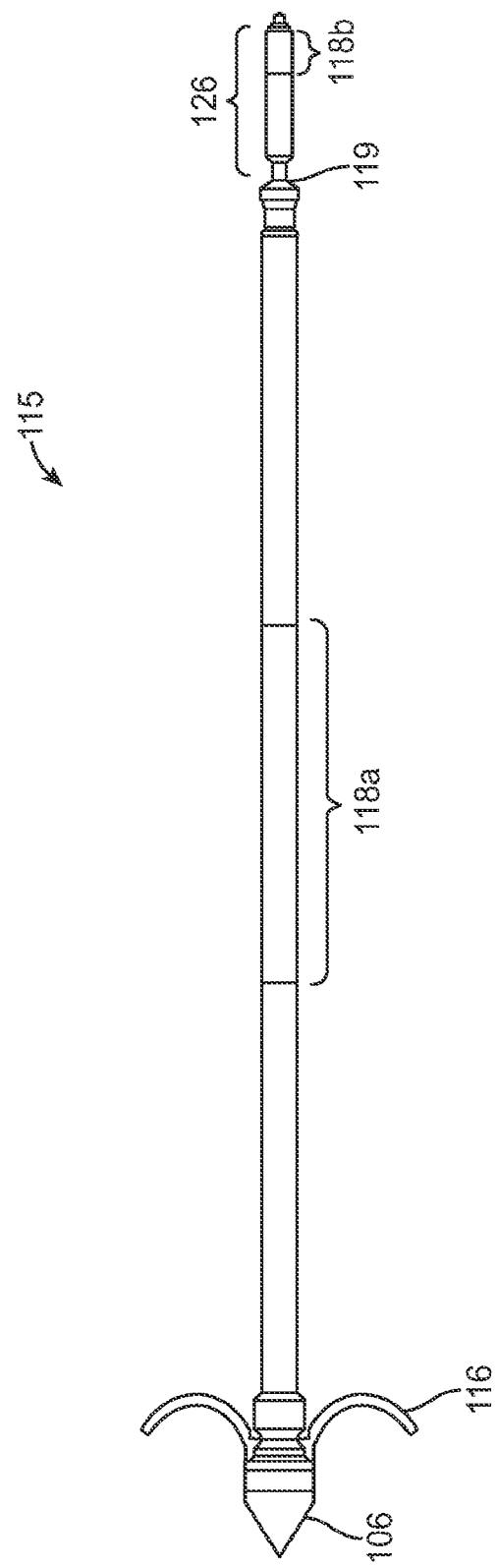

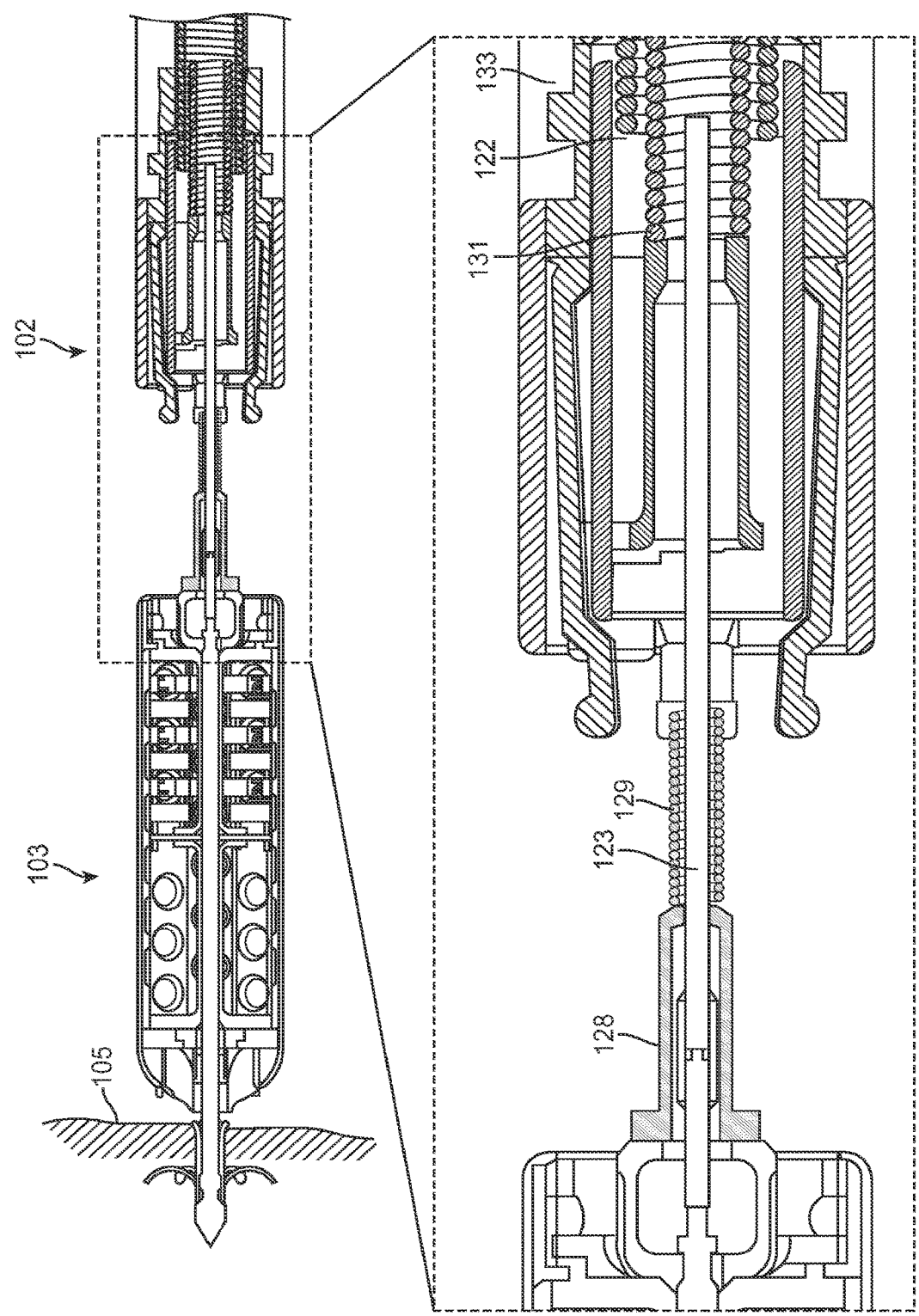

TEMPORARY ELECTRODE CONNECTION FOR WIRELESS PACING SYSTEMS

CROSS-REFERENCES TO RELATED APPLICATIONS

The present application is a divisional of U.S. patent application Ser. No. 12/890,308, now U.S. Pat. No. 9,283,392), filed Sep. 24, 2010, which is a continuation of International Patent Application No. PCT/US2009/037978, filed Mar. 23, 2009, which claims the benefit of provisional U.S. Application No. 61/039,335, filed Mar. 25, 2008, the full disclosures of which are incorporated herein by reference.

BACKGROUND OF THE INVENTION

1. Field of the Invention

The field of the present invention relates generally to implanted devices for tissue stimulation, monitoring, and other therapeutic or diagnostic functions, and specifically to implantable devices for the stimulation of cardiac tissue, for example pacemakers or implantable cardioverter-defibrillators (ICDs). More specifically, it pertains to such devices utilizing wireless energy transfer, for example using ultrasound energy.

2. Description of the Background Art

Pacemakers provide electrical stimulus to heart tissue to cause the heart to contract and hence pump blood. Conventionally, pacemakers include a pulse generator, typically implantable in a patient's pectoral region, with one or more leads (wires) extending from the pulse generator into a heart chamber. The lead terminates at an electrode, which is implanted in the heart.

While pacemakers using leads are widely used, they have several drawbacks. For example, the gradual intertwining of leads with heart tissue over time secures the lead in place but also hinders lead removal or repositioning. Another drawback to using leads is the limit placed on the number of heart sites that may be stimulated. While pacing at multiple sites may be beneficial for treating different heart conditions such as congestive heart failure, arrhythmia and atrial fibrillation, using multiple leads may block a clinically significant fraction of the cross section of the veins and cavities through which the leads are routed.

Pacing systems using wireless electrodes have been suggested as a way of overcoming the limitations of conventional systems with leads, with wireless receiver-stimulator electrodes implanted into the heart wall and in wireless communication with transmitter(s) for energy delivery or for communication of control or feedback signals. The inventors of this patent application have proposed systems using implantable wireless electrodes that receive acoustic energy and convert it into electrical energy for electrically stimulating the heart. Such methods and systems have been disclosed in co-pending U.S. Patent Application Nos. (Publication No.) 20060136004, 20060136005, 20070027508, 20070055184, 20070078490 and 20070060961 and Ser. No. 11/752,775, which are herein incorporated by reference in their entirety. As another example, U.S. Patent Application No. (Publication No.) 2006/0085039 discloses a system using implantable wireless electrodes that receive energy via inductive coupling of a coil in the electrode to a radio frequency antenna attached to a central pacing controller.

When implanting a wireless receiver-stimulator, the choice of the implantation location is important for at least two reasons. First, it is desirable that the tissue in electrical contact with the stimulation electrodes of the receiver-stimulator be sufficiently excitable to allow efficient pacing stimulation by the receiver-stimulator. Secondly, it is desirable that the wireless receiver-stimulator be positioned relative to the wireless transmitter to allow efficient wireless communication between the two, particularly with respect to energy transmission and reception.

While the determination of the location in conventional systems with leads involves fairly straightforward techniques, such techniques do not translate directly for wireless pacing systems. In a conventional pacing system, determination of an excitable tissue location is customarily practiced by monitoring electrogram (EGM) signals at the implantation site and additionally by stimulating or pacing through the electrodes, before permanently implanting them in the patient. The user simply connects the proximal end of the pacing lead into a pacemaker programmer or other electrophysiology instrumentation that allows the user to monitor EGM signals from the electrodes on the lead and to stimulate through the electrodes on the lead to confirm that the implant location is appropriate.

In contrast, in a wireless system one obstacle is the lack of a direct connection to one or more of the electrodes for the monitoring of EGM signals. Additionally, stimulating through the wireless electrodes involves transmission of energy from a transmitter to a receiver-stimulator through a wireless process, whether for charging the receiver-stimulator or for transduction from wirelessly delivered energy to stimulation energy. This lumps two effects together: the efficiency of the wireless transfer of energy (by whatever means the system employs, such as acoustic energy, radio frequency (RF), or other means) and the properties and excitability of the tissue that the pacing electrodes are placed over. This could result in user confusion and potentially inaccurate determination of pacing thresholds and energy conversion efficiencies.

For example, in a conventional pacing system with leads, a high pacing threshold implies a poor location for placing the pacing electrodes. This may indicate, for example, that the electrodes are not in close proximity to the tissue or are placed over non-excitable tissue. A straightforward resolution of this problem is moving the electrode until an appropriate location is found. In contrast, in a wireless system a high energy level that is required to pace could be the result of inefficient or poor wireless transfer of energy from the transmitter to the receiver-stimulator, or, similar to the conventional pacing system, the result of a poor location of the receiver-stimulator not in close proximity to the tissue or over non-excitable tissue.

An extension of the above lead-based techniques to wireless stimulation systems comprises establishing electrical contact between one or more of the electrodes of an implantable wireless receiver-stimulator, a delivery system (such as a catheter or the like), and the tissue. Alternatively, surrogate electrodes on the delivery system, i.e., not the electrodes of the wireless receiver-stimulator, may be used for assessing whether the tissue is excitable. However, it requires the use of one or more of the electrodes of the implantable wireless receiver-stimulator to fully assess the efficient and effective transfer of energy to the receiver-stimulator from the transmitter. The desirable approach is to use one or more of the electrodes of the implantable wireless receiver-stimulator to sense local tissue EGMs in order to (1) determine a suitable implant location, as well as (2) determine efficiency of energy conversion by the wireless implant. For example, such a technique is partially suggested in the above referenced U.S. Patent Application (Publication No.) 2006/0085039. Another approach to determine the appropriate location for implantation of the electrodes is to observe the hemodynamic parameters of the heart upon stimulating a location. Such an approach is described in the Applicants' co-pending U.S. Patent Application (Publication No.) 2007/0060961. While this desirable approach may be constructed, it does give rise to a number of challenges.

First, once the wireless electrode is implanted, disconnected from the delivery system, and the delivery system is removed, any conductive material at the severed connection on the wireless implant, remaining exposed after disconnecting the delivery system from the electrode(s), presents a potential alternate electrical path between the implant electrodes and the exposed remains, allowing some or all of the stimulation current to bypass the desired stimulation path and thereby reduce or entirely undermine stimulation effectiveness.

Second, it is also desirable to be able to assess conversion efficiency in-situ, perhaps over a variety of energy transmission conditions. It would be desirable to perform this assessment while directly connected to one or more of the electrodes without requiring that the wireless implant deliver electrical output (stimulation energy) at sufficient strength to capture tissue. By monitoring the electrical energy output, the efficiency of transmission can be assessed and the likelihood of pacing capture can be correlated with the efficiency.

Therefore, it is desirable to have a wireless pacing system that allows the user to determine a suitable implant location and assess the efficiency of energy conversion prior to permanent implantation by using the pacing electrodes of the receiver-stimulator, and further eliminate exposed residual conductive material after removal of the delivery system.

BRIEF SUMMARY OF THE INVENTION

Embodiments of the present invention are directed to wireless receiver-stimulator devices for cardiac stimulation. An implantable wireless receiver-stimulator is implanted into a location in the heart using a delivery system, which typically comprises a delivery catheter but may take other forms as well. The receiver-stimulator comprises a cathode and an anode, and is configured to receive energy delivered by a controller-transmitter. The receiver-stimulator converts the energy to electrical energy and delivers the electrical energy as pacing pulse (stimulation) energy, through the cathode and anode stimulation electrodes, which stimulates the heart. By practice, the cathode is typically the P− and the anode is typically the P+ for the stimulation electrodes.

The delivery system comprises conductive wires routed through the catheter which temporarily connect one or more of the electrodes of the receiver-stimulator to an external monitor and pacing controller. A first temporary electrical connection connects the delivery system with the receiver-stimulator's cathode, and a second temporary electrical connection connects the delivery system with the receiver-stimulator's anode. The system may be operated with a single temporary connection, preferably to the cathode, and an indifferent electrode, which may be a separate electrode acting as the anode (apart from the anode of the receiver-stimulator) that is integrated into the delivery system or on a separate device, or still further a body surface electrode. Temporary electrical connections allow the user to monitor the heart's electrical activity at a location in the heart as sensed by the receiver-stimulator's cathode and anode and determine whether the location indicates excitable heart tissue. Alternatively, combination of the temporary electrical connection between the receiver-stimulator's cathode and a monitoring system and a permanent electrical connection between the indifferent electrode and the monitoring system can also be used to determine whether the location indicates excitable heart tissue.

Once a receiver-stimulator is positioned at a heart location intended as the implant location, the heart tissue is stimulated using electrical stimulation energy from an external pacing controller delivered to the tissue through the receiver-stimulator's cathode and an anode via the temporary electrical connection(s), thereby allowing determination of an acceptable electrical pacing threshold at the location of the cathode prior to permanent attachment of the wireless receiver-stimulator to the heart wall.

The temporary electrical connection can also be used to determine the efficiency of conversion of energy to electrical stimulation energy by the receiver-stimulator at a given location in the heart. In one embodiment, this is accomplished by delivering acoustic energy from a wireless controller-transmitter or similar implantable or externally-applied acoustic transmitter to the wireless receiver-stimulator, converting the acoustic energy to electrical energy, and delivering electrical energy to the heart tissue through the receiver-stimulator's cathode and an anode, while monitoring the electrical energy using an external monitor connected to the electrodes via the temporary electrical connections through the delivery system. The electrical energy in this embodiment need not be at pacing strength, since conversion efficiency can be gauged even at lower energy levels. In an alternative embodiment, the heart is stimulated at pacing strength using the electrical energy that was converted from the acoustic energy, and the EGM generated by the stimulation of heart tissue is monitored using the temporary electrode connections on the receiver-stimulator or other electrodes, e.g., surface EKG electrodes or other electrodes mounted on the delivery system.

When a suitable implantation location is determined, the wireless receiver-stimulator is attached to the heart wall and the temporary electrical connections are disconnected using a disconnect mechanism. The disconnect mechanism is configured to prevent the creation of an unwanted secondary set of conductive areas on the receiver-stimulator.

In one embodiment, the disconnect mechanism seals an electrical contact point of the cathode temporary electrical connection on the receiver-stimulator from patient fluid or tissue. In another embodiment, the disconnect mechanism comprises a magnetically operated switch which opens when the delivery system is detached from the receiver-stimulator, thereby internally disconnecting the cathode temporary electrical connection contact point on the receiver-stimulator from the active electrodes of the receiver-stimulator. In other embodiments, the disconnect mechanism comprises bellows configured to stretch and disconnect the cathode temporary electrical connection when the delivery system is disconnected, or a conductive dome structure configured to pop out and disconnect the cathode temporary electrical connection when the delivery system is pulled away and disconnected.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 2b is a diagrammatic view of a needle assembly.

FIG. 2f is a cross sectional view of a wireless cardiac stimulation device and a delivery system in a tethered state.

DETAILED DESCRIPTION OF THE INVENTION

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments. In general, features described in one embodiment might be suitable for use in other embodiments as would be apparent to those skilled in the art.

A wireless cardiac stimulation system is disclosed that allows the user to assess tissue viability for excitation at a location in the heart, determine an acceptable electrical pacing threshold at the location, and determine operational efficiency of a wireless cardiac stimulation system at the location, prior to permanent implantation of the wireless pacing device.

Figure 1A:
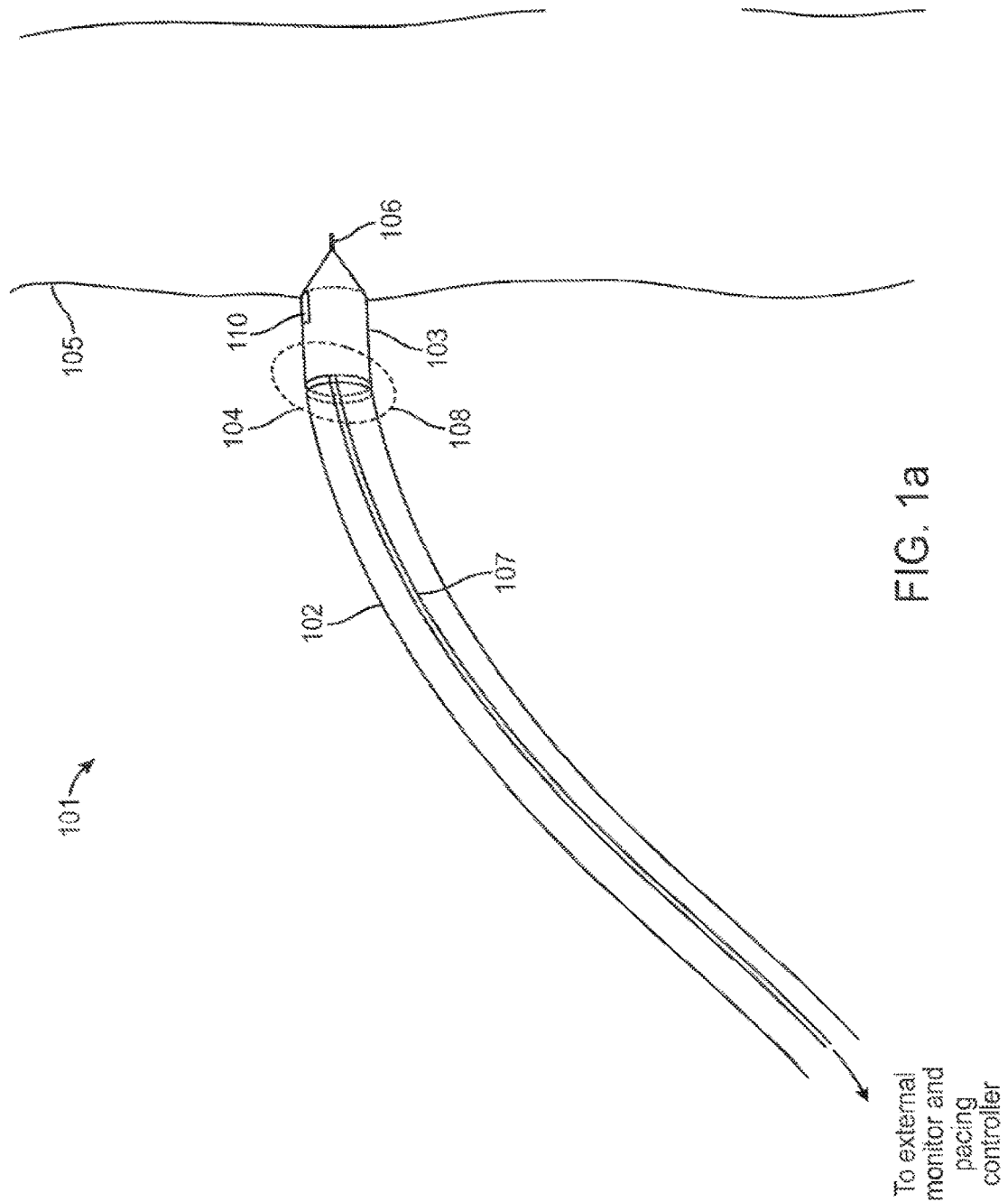
FIGS. 1a-1c are diagrammatic views of a wireless cardiac stimulation device and a delivery system.
Figure 1B:
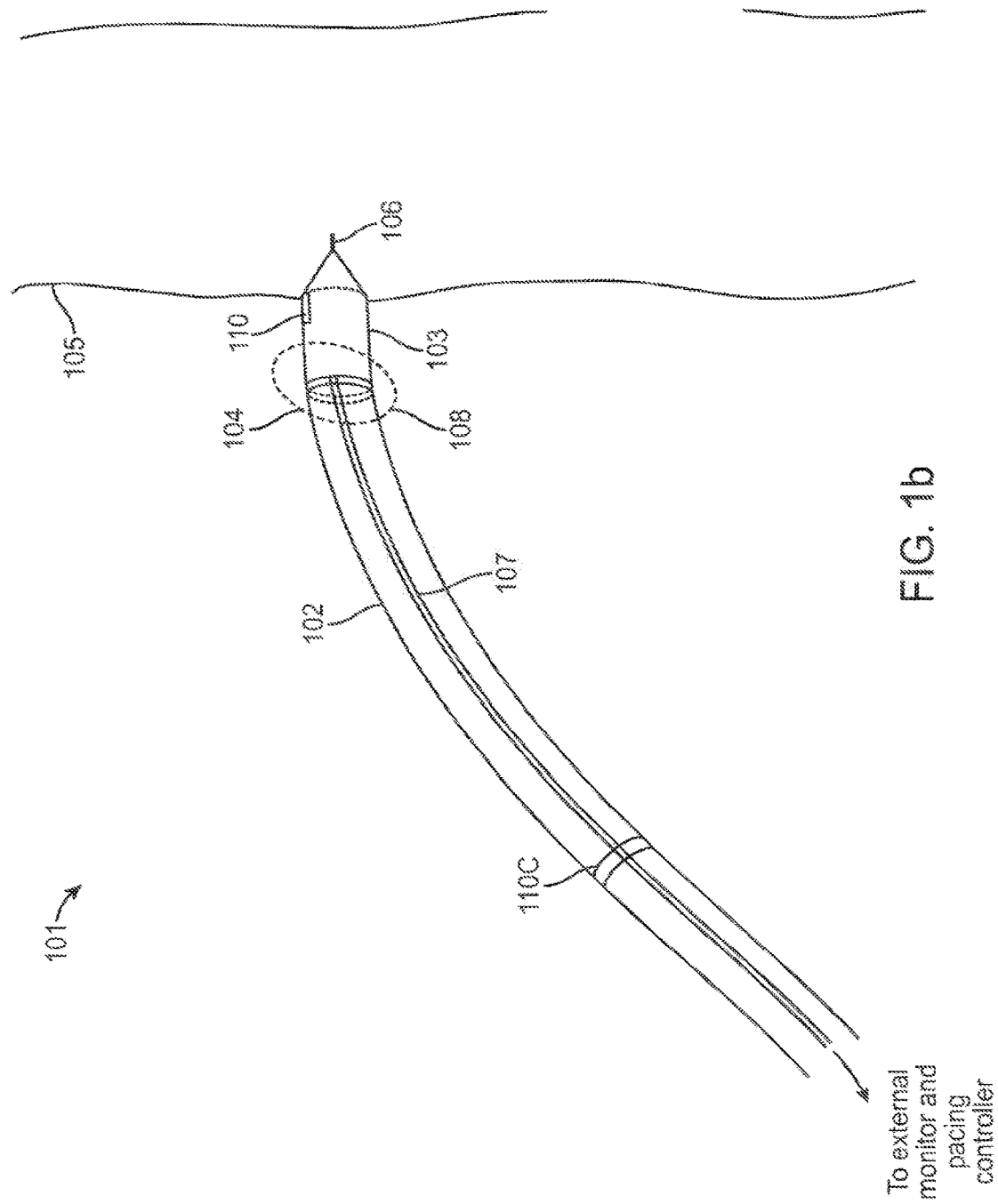
Figure 1C:
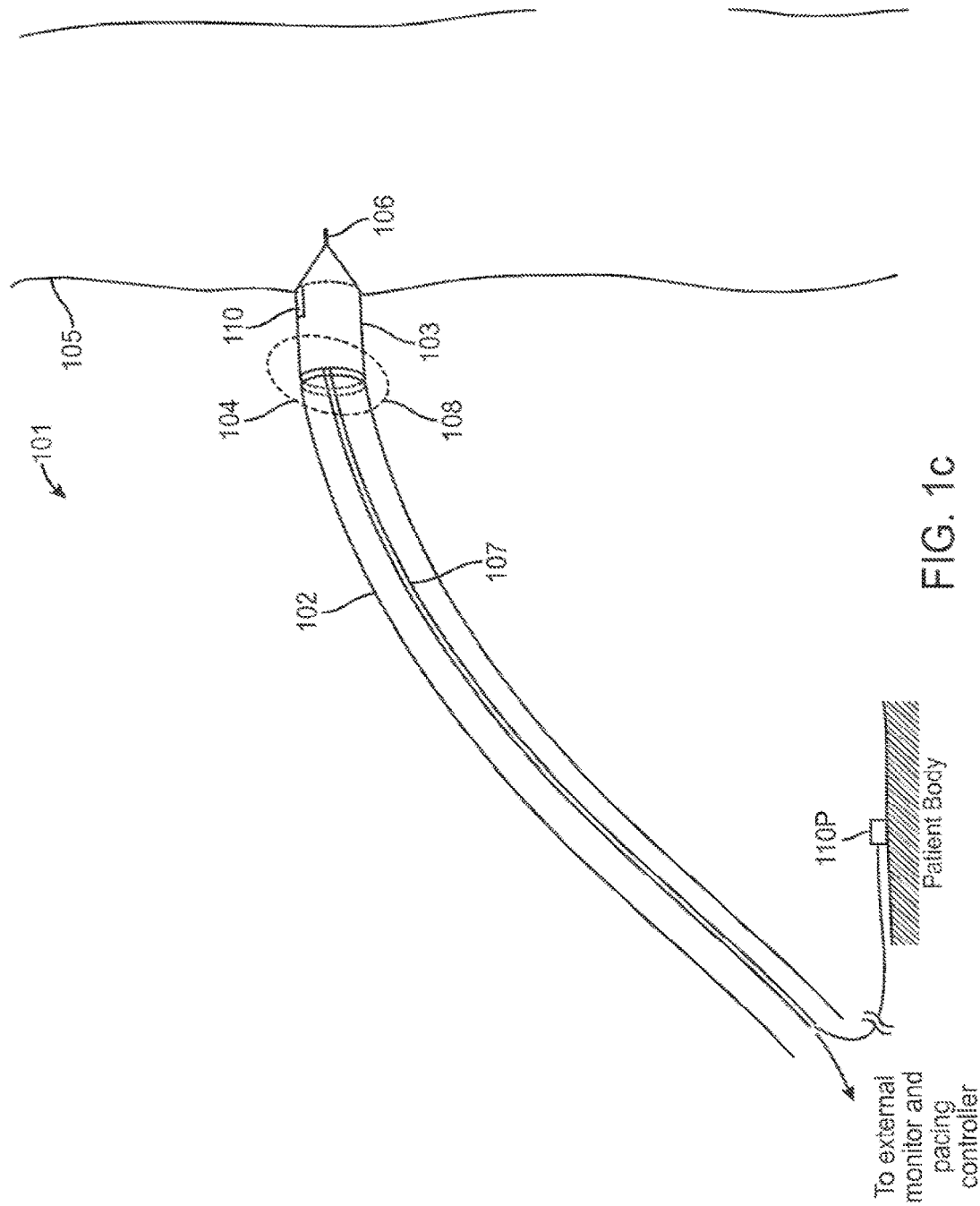

FIGS. 1a-1c are diagrammatic views of a wireless cardiac stimulation system 101, in accordance with an embodiment of the present invention. A delivery system 102 with a wireless receiver-stimulator (hereinafter also abbreviated as "R-S") 103 attached to the delivery system's distal tip 104 is inserted into the body of a patient. Typically, this would be through vascular access through the groin. Other entry sites sometimes chosen are found in the neck and are in general well known by physicians who practice such medical procedures.

The delivery system 102 is positioned so that the R-S 103 at the distal tip 104 of the delivery system 102 is appropriately situated on a part of the heart wall 105 where the R-S 103 is to be attached/implanted. The insertion of the delivery system 102 may be facilitated by the use of a guidewire and/or a guiding catheter, as is known in the art. In addition, the movement of the delivery system 102 may be monitored fluoroscopically.

The wireless R-S 103 comprises a cathode 106 and an anode 110 for stimulating patient tissue, with the cathode 106 located at the distal tip of the R-S 103. The cathode is intentionally designed with a smaller surface area relative to the anode. This leads to higher current densities at the cathode, resulting in tissue stimulation at the cathode. Hence, the term cathode and stimulation electrode are interchangeably used. Additionally, the delivery system 102 comprises two temporary electrical connections between the R-S 103 and the delivery system 102: a first temporary electrical connection for establishing electrical contact with the cathode 106 and a second temporary electrical connection for establishing electrical contact with the anode 110. Alternatively, this may take the form of a single temporary electrical connection for establishing contact with the cathode 106 and the second electrical connection provided by an indifferent electrode 110C configured onto the delivery system (see FIG. 1b) or an indifferent electrode 110P that is configured to be in electrical contact with the patient's body that is remote from the delivery system (see FIG. 1c), wherein this second electrical connection is not temporary electrical connection. The temporary electrical connections comprise electrical contact points between the proximal end of the R-S 103 and the distal end of the delivery system 102. Specifically, the first temporary electrical connection (for the cathode) is between a first electrical contact point on the proximal end of the R-S 103 and a first electrical contact point on the distal end of the delivery system 102. Similarly, the second temporary electrical connection (for the anode) is between a second electrical contact point on the proximal end of the R-S 103 and a second electrical contact point on the distal end of the delivery system 102. The temporary electrical connections provide conductive paths from the cathode 106 and anode 110 of the R-S 103 to an external monitor and pacing controller via conductive wires 107 routed through the delivery system 102, allowing externally controlled monitoring and pacing. Once the R-S 103 is permanently attached to patient tissue, the R-S 103 detaches from the delivery system 102 and the temporary electrical connections are disconnected.

It is noted that on the R-S 103, any metal or conductive material on the cathode's temporary electrical connection contact point that remains exposed after the R-S 103 detaches from the delivery system 102 presents a potential for an alternate electrical path between the remaining conductive material and the anode. This could allow some or all of the stimulation current to bypass the desired path between the cathode 106 at the distal tip of the R-S 103 and the anode 110, at best reducing the efficiency of the wireless R-S 103 and at worst shunting energy away from the tissue and rendering the wireless R-S 103 ineffective. Therefore, various disconnect mechanisms for the cathode's temporary electrical connection are disclosed herein which isolate one or more electrical contact points of the cathode's temporary electrical connection on the wireless R-S 103. One particular embodiment comprises using a non-hermetically sealed enclosure around the cathode's temporary electrical connection contact point on the R-S 103. Another embodiment comprises using magnetic and/or mechanical switches internal to the R-S 103 for electrically isolating the cathode's temporary electrical connection contact point from the cathode itself. These and other embodiments are described in more detail below. The R-S 103 and the delivery system 102 will now be described in more detail.

Figure 2A:
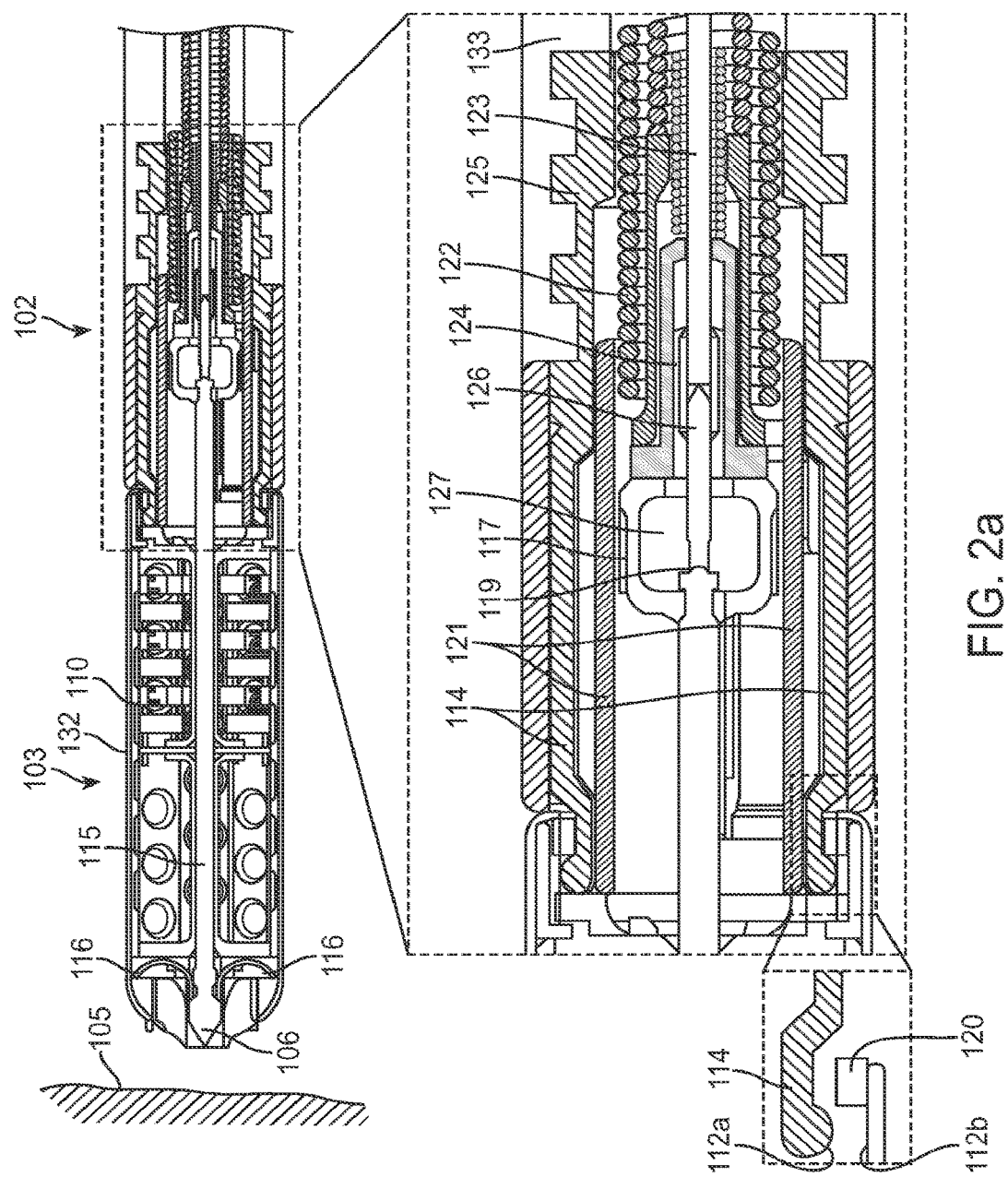
FIG. 2a is a cross sectional view of a wireless cardiac stimulation device and a delivery system in a retracted state.

FIG. 2a shows a cross sectional view of a wireless R-S 103 attached to a delivery system 102, in accordance with an exemplary embodiment of the present invention. The wireless R-S 103 comprises a needle assembly 115 (also called an axle assembly), also shown in FIG. 2b. The needle assembly 115 has a cathode 106 at its distal tip for stimulating the heart tissue. The needle assembly 115 is coated with an insulating layer, such as a thin ceramic layer, except at the cathode 106, at a segment 118a (shown in FIG. 2b) to allow for an electrical path from the internals of the R-S 103 to the cathode 106 via the needle assembly 115, and at a proximal segment 118b (shown in FIG. 2b) to allow for an electrical path from the delivery system 102 to the cathode 106 via the needle assembly 115. The needle assembly 115 further comprises a neck 119 configured to snap and disconnect as the delivery system 102 disengages from the R-S 103.

FIG. 2a shows the needle assembly 115 in a retracted state, with the cathode 106 fully within the R-S 103. The needle assembly 115 comprises one or more barbs 116 coupled proximal to the cathode 106. The barbs 116 are released when the needle assembly 115 is pushed sufficiently distally outward from the R-S 103 towards the heart wall 105. The distal portion of the delivery system 102 is shown in an enlarged view in the bottom panel of FIG. 2a. A conductive wire 123 in the delivery system 102 is coupled to a proximal segment 126 of the needle assembly 115 by a connecting collar 124.

The outside of the wireless R-S 103 housing serves as an anode 110 for stimulating the heart tissue. The anode 110 may comprise only a portion of the R-S 103 housing, or it may comprise the entire outer surface of the R-S 103 housing. The R-S 103 preferably comprises an endothelial growth promoting covering 132 which does not insulate the surface of the anode 110. For example, in one embodiment the covering 132 may comprise a polyester mesh.

The delivery system 102 comprises a flexible outer sheath 133 connected to a rigid collar 125 with flexible extensions or fingers 114. The fingers 114 are held by tubular extension 121 radially outwards into place around an indentation 120 of the R-S 103, thereby detachably attaching the delivery system 102 to the R-S 103. In one embodiment, the fingers 114 are made of a superelastic material, such as Nitinol, and configured to collapse radially inwards in the absence of a restrictive force and thereby release the R-S 103. Alternatively, the fingers 114 may comprise stainless steel, since it is contemplated that the strains experienced by such fingers 114 are small. A tubular extension 121 attached to the distal end of a retractable flexible wire coil 122 inside the sheath 133 provides such a restrictive force and holds the fingers 114 radially extended, preventing them from collapsing. To release the delivery system 102 from the R-S 103, the wire coil 122 and its tubular extension 121 are retracted, thereby allowing the fingers 114 to collapse and release the R-S 103.

Once the delivery system 102 has been maneuvered into place within the heart chamber, the wireless R-S 103, being disposed at the distal end of the delivery system 102, comes close to or contacts the heart wall 105 such that the cathode 106 is in electrical contact with the heart wall 105. The anode 110 may be in contact with the heart wall 105 or it may remain within the chamber of the heart. Alternatively, any other indifferent electrode (110C or 110P), e.g., one positioned on the outer sheath of the delivery system 102 or placed on the patient's body remote from the delivery system, respectively, may be used as an anode. The wireless R-S 103 can thus be repositioned by the delivery system 102 to assess electrical activity at various locations of the heart wall 105 using the cathode 106 and the anode 110 or indifferent electrode 110C or 110P.

During the implantation of the wireless R-S 103, temporary electrical connections from the delivery system 102 to the wireless R-S 103 electrodes are provided, one for the cathode 106 and one for the anode 110. The exploded view in the bottom panel in FIG. 2a shows one or more electrical contact points 112a at the distal end of the delivery system 102 and one or more electrical contact points 112b at the proximal end of the R-S 103, where the anode 110 of the R-S 103 comes into electrical contact with one or more fingers 114 of the delivery system 102 to form a temporary electrical connection for the anode 110. Note that the contact points 112a and 112b are shown apart in the enlarged view of FIG. 2a for illustration purposes only, as they are actually in contact in the particular configuration of the R-S 103 shown in FIG. 2a. One or more conductive wires coupled to the fingers 114, provide a conductive path from the anode 110 to an external monitor or controller via the delivery system 102. Optionally, these wires may also serve as articulation control wires. Alternatively, the rigid collar 125 makes electrical contact with the tubular extension 121 of flexible coil 122 which in turn provides a conductive path from anode 110 to an external monitor or controller via the delivery system 102. In one embodiment, the R-S 103 and the fingers 114 are gold plated at the temporary electrical contact points 112 in order to provide increased electrical conductivity.

While a direct temporary electrical connection is provided from the delivery system 102 to the anode 110 as described above, it is contemplated that a direct connection from the delivery system 102 to the cathode 106 located at the distal tip of the wireless R-S 103 may provide alternative current paths, or may impose complications in manufacturing, cost or reliability. Thus, a temporary electrical connection between the distal end of the delivery system 102 and the proximal end of the wireless R-S 103 housing is disclosed herein that provides a conductive path from the distal tip of the delivery system 102 via the needle assembly 115 to the cathode 106.

In one embodiment, this temporary electrical connection to the cathode 106 comprises an enclosure 117 configured around the neck segment 119 of the needle assembly 115. At its distal end, the enclosure 117 is tightly coupled to the needle assembly 115. Internally, the enclosure 117 comprises a seal 127 around the proximal segment 126 of the needle assembly 115. The seal 127 may be made of silicone, rubber or other flexible insulating material. The seal 127 need not necessarily be hermetic, but it is configured to provide high enough electrical resistance, for example in excess of 10,000 ohms, between the detached temporary electrical connection and the heart wall 105 or the fluid within the heart chamber to allow substantially any electrical current applied to the needle 115 to flow through the electrical path of the cathode 106 to the anode 110.

When the R-S 103 is permanently attached to the heart wall 105 and the delivery system 102 is to detach from the R-S 103, the conductive wire 123 is retracted into the delivery system 102, breaking the needle assembly 115 at the neck 119 and removing the proximal segment 126 of the needle assembly 115 from the enclosure 117. In such an embodiment, the two end points of the broken neck represent the two temporary electrical contact points for the temporary electrical connection between the catheter and the cathode. Upon removal of the proximal segment 126 from the enclosure 117, the seal 127 closes in around the hole left by the removed proximal segment 126, electrically isolating the remaining part of the needle assembly 115 (which includes the cathode temporary electrical connection contact point on the R-S 103) inside the sealed enclosure 117 from patient fluid and tissue.

Figure 2C:
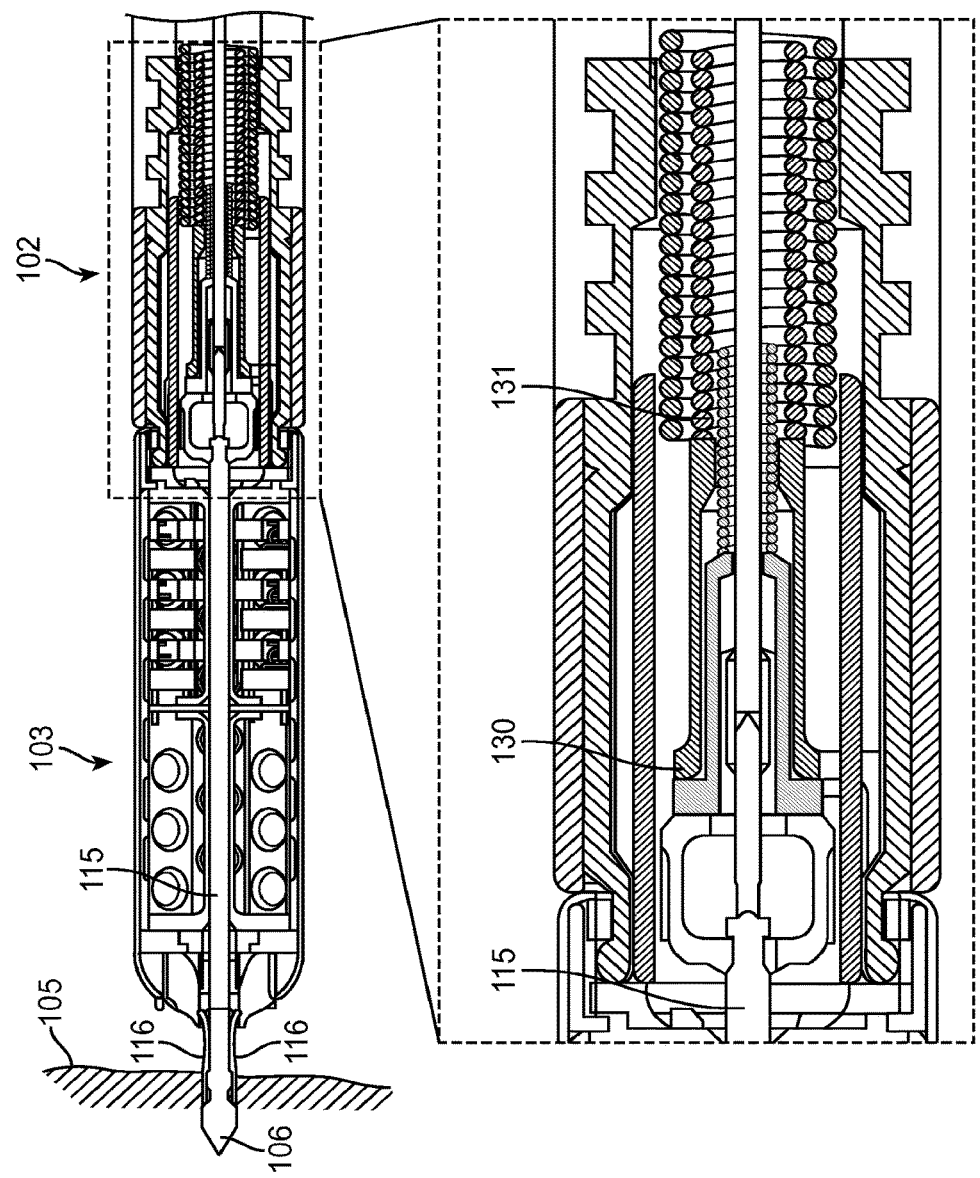
FIG. 2c is a cross sectional view of a wireless cardiac stimulation device and a delivery system in an injected state.
Figure 2D:
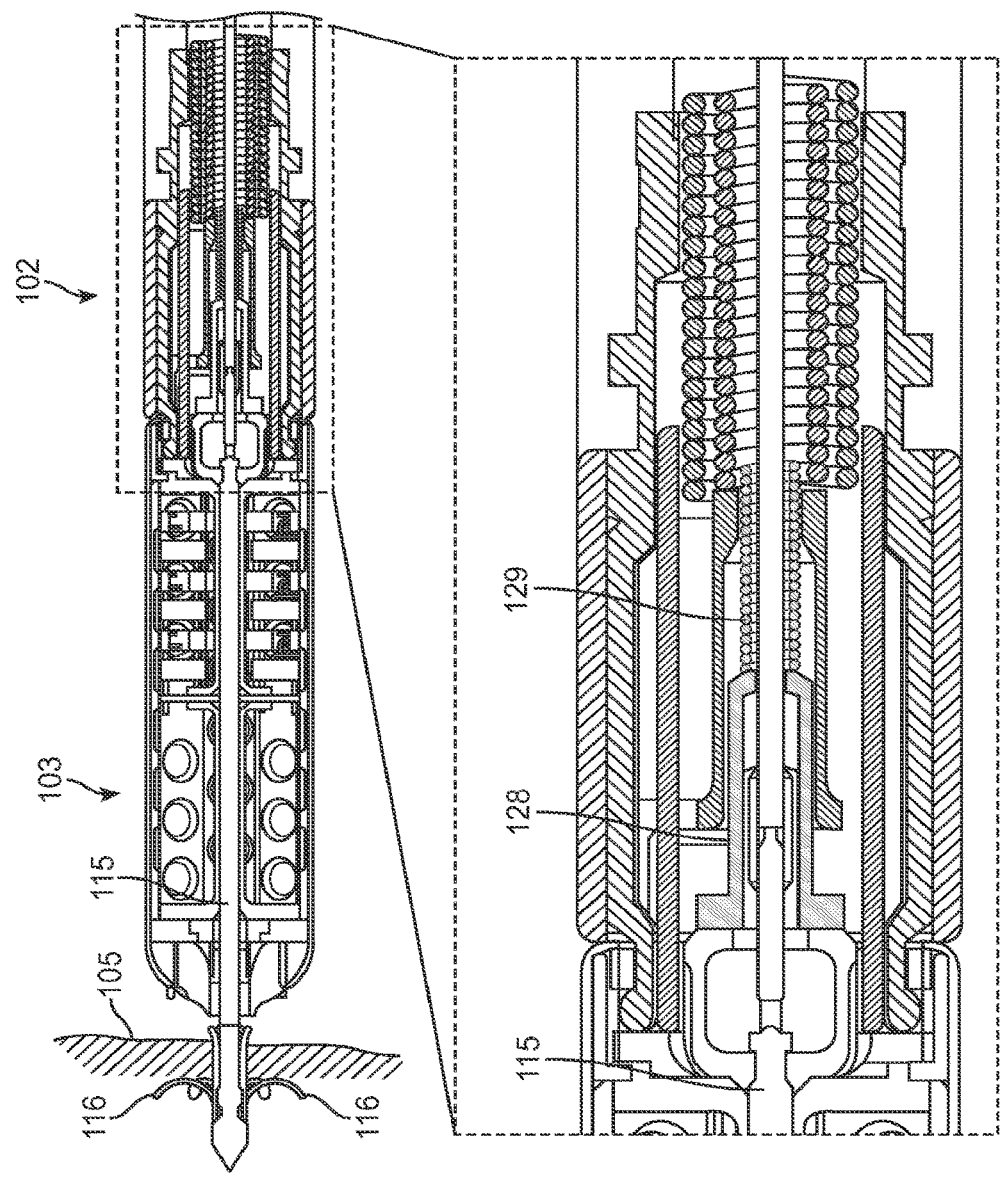
FIG. 2d is a cross sectional view of a wireless cardiac stimulation device and a delivery system in a triggered state.

We now turn to describing a sequence of states for the R-S 103 as it goes from introduction into the patient to final attachment to the heart wall 105. This sequence is shown in FIGS. 2a-2h. In FIG. 2a ("retracted state"), the R-S 103 is initially introduced into the patient. The R-S 103 is attached to the delivery system 102 and the needle assembly 115 is in a retracted state. In FIG. 2c ("injected state"), a wire coil 131 and its extension 130 have pushed the needle assembly 115 distally with respect to the body of the R-S 103, injecting the cathode 106 into the patient's heart wall 105 but without releasing the barbs 116. The distal mechanism of the catheter is such that the extension 130 is limited in its travel so that movement of the wire coil 131 cannot move the needle assembly 115 into its triggered state, thereby obviating requirements for precise motion in the handle of the delivery system 102. In FIG. 2d ("triggered state"), a wire coil 129 and its extension 128 have pushed the needle assembly 115 further out, releasing the barbs 116 and allowing the R-S 103 to securely attach itself to the heart wall 105.

Figure 2E:
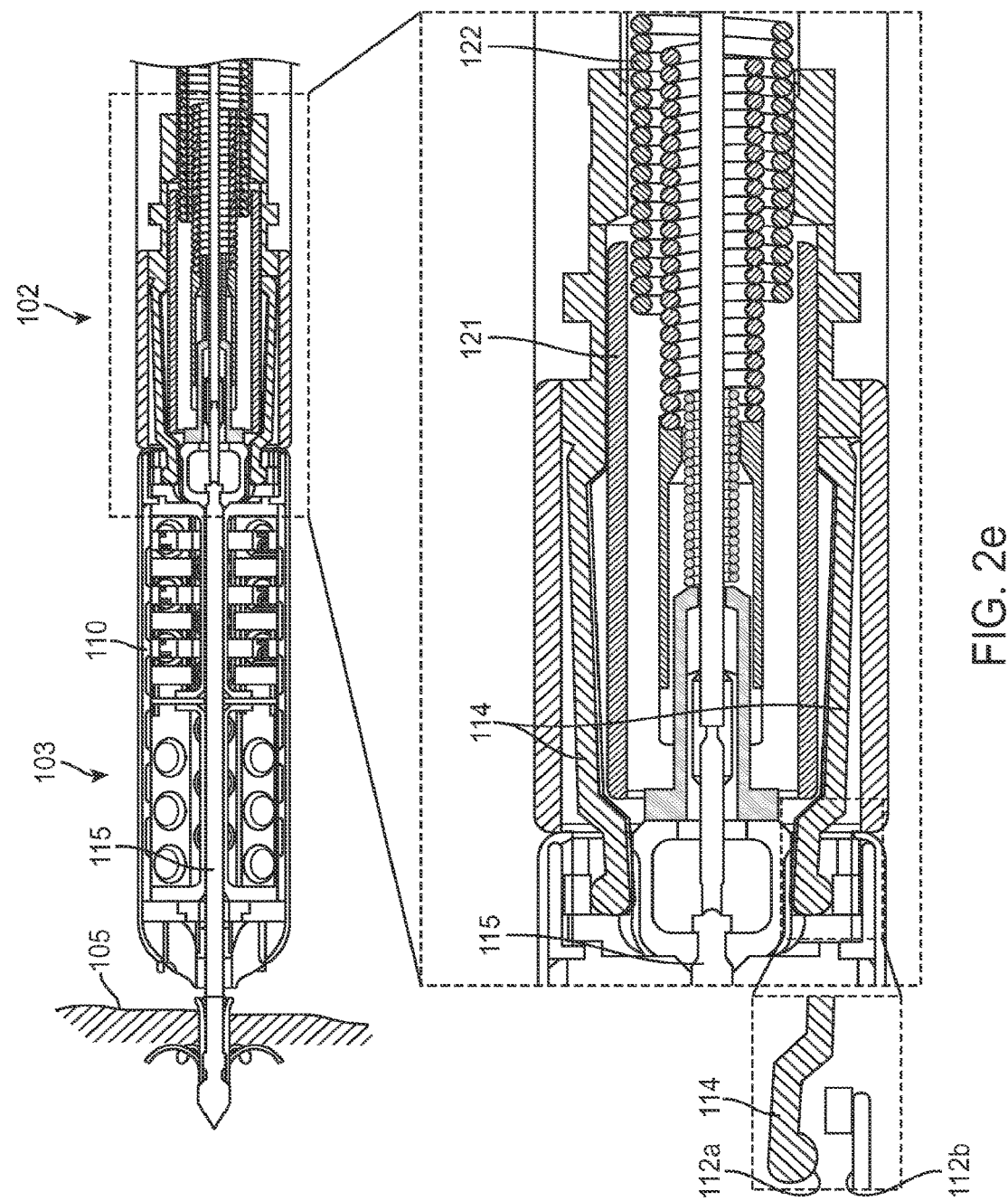
FIG. 2e is a cross sectional view of a wireless cardiac stimulation device and a delivery system in a released state.

In FIG. 2e ("released state"), the wire coil 122 and its extension 121 are retracted into the delivery system 102, thereby allowing the fingers 114 to radially collapse inwards and release the R-S 103. At this point, the temporary electrical connection for the anode 110 is disconnected, as the contact points 112a on the one or more fingers 114 of the delivery system 102 disconnect from their corresponding contact points 112b on the R-S 103.

Figure 2G:
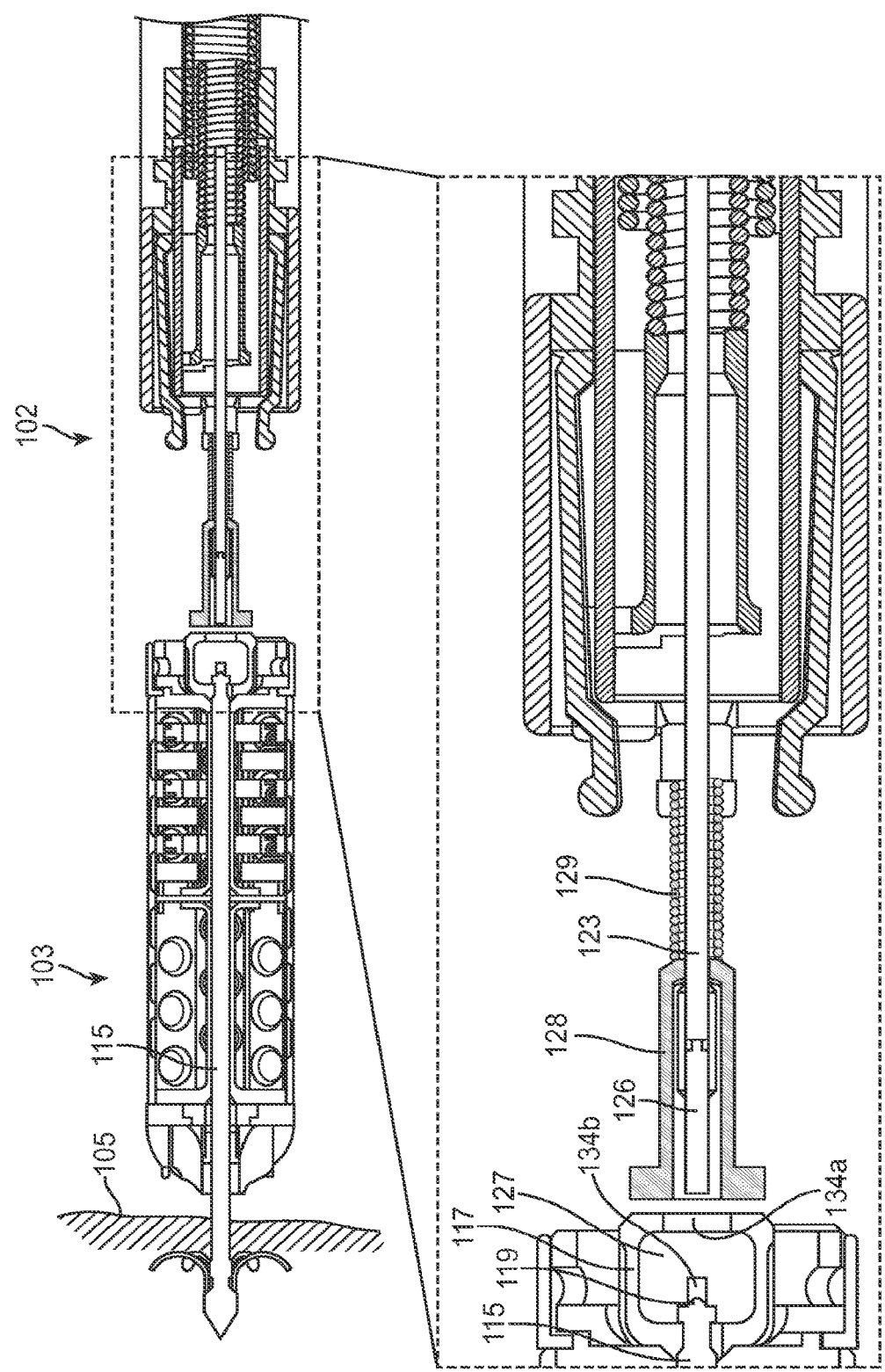
FIG. 2g is a cross sectional view of a wireless cardiac stimulation device and a delivery system in a tether broken state.
Figure 2H:
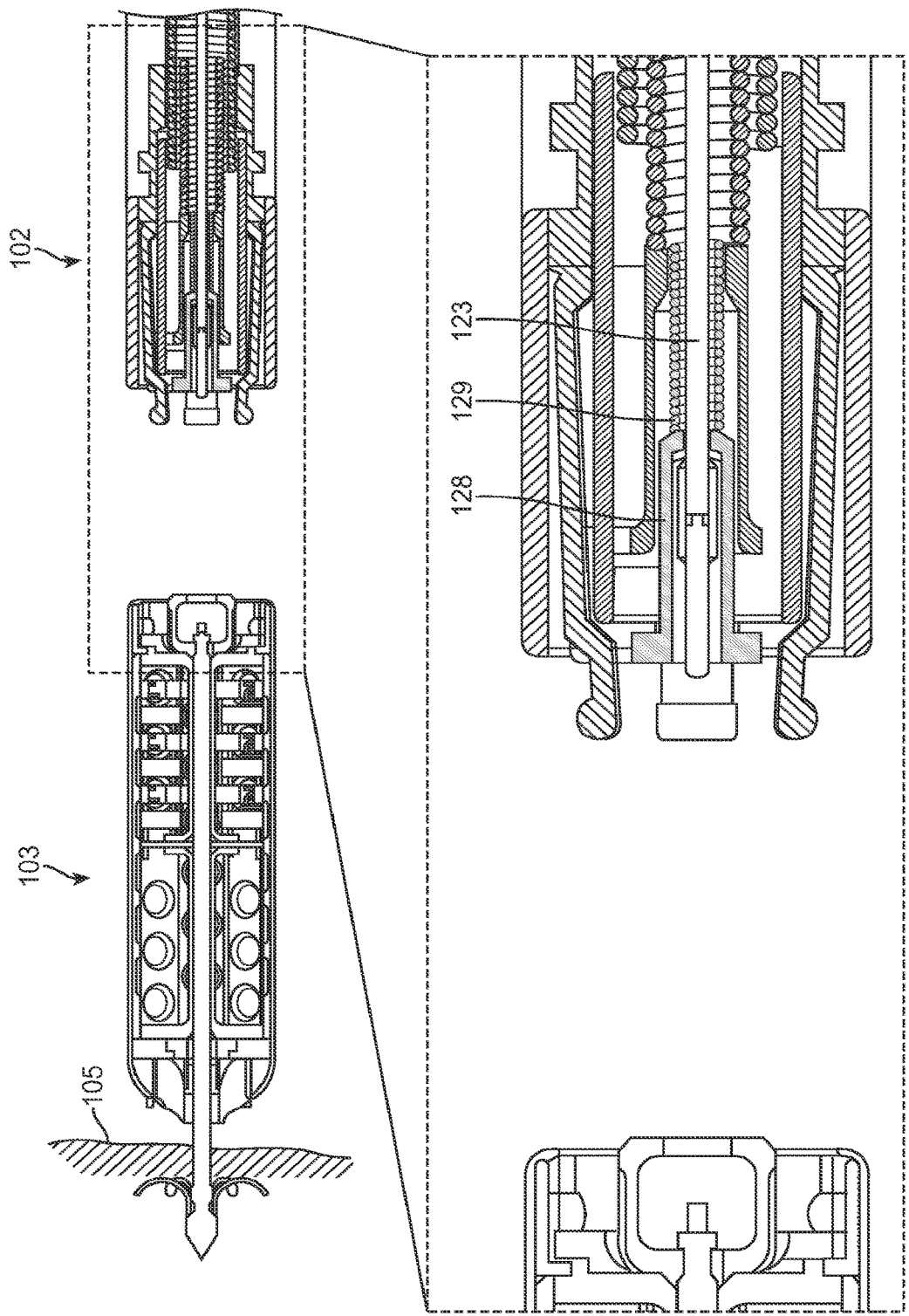
FIG. 2h is a cross sectional view of a wireless cardiac stimulation device and a delivery system in a delivered state.

In FIG. 2f ("tethered state"), the catheter sheath 133 and wire coils 122 and 131 are retracted and/or the wire coil 129 and wire 123 are extended, leaving the R-S 103 tethered to the wire 123 and in contact or in proximity with the tubular extension 128 of the wire coil 129. The tethered state allows the R-S 103 to remain attached to the delivery system 102 and retrievable, while being only connected by a very flexible coupling. This flexibility allows the R-S 103 to move with the heart wall independently of the delivery system 102, demonstrating under flouroscopic visualization that the R-S 103 is reliably attached to the heart wall 105. Additionally, the delivery system 102 and the tethering mechanism can be moved by small amounts, changing the degree of slack without eliminating slack. Such movement may demonstrate that the attachment point of the R-S 103 to the heart wall remains fixed while the orientation of the R-S 103 with respect to the heart wall varies, further indicating reliable attachment. In FIG. 2g ("tether broken state"), the wire 123 is retracted while the wire coil 129 and its extension 128 exert a resistance against the R-S 103 and prevent it from being pulled along. This causes the needle assembly 115 to break at the neck 119. The two end points of the broken neck 119 represent the two temporary electrical contact points for the temporary electrical connection between the delivery system 102 and the cathode 106, with contact point 134a representing the electrical contact point at the distal end of the delivery system 102 and contact point 134b representing the electrical contact point at the proximal end of the R-S 103. As the wire 123 continues to retract, it removes with it the broken proximal piece 126 of the needle assembly 115 from the enclosure 117. Seal 127 closes following the removal of proximal piece 126, forming an electrical isolation between needle 115 and the fluid surrounding the proximal end of the R-S 103. In FIG. 2h ("delivered state"), the wire coil 129 and its extension 128 are retracted into the delivery system 102 along with the wire 123, leaving the R-S 103 delivered in the heart wall 105.

Figure 3:
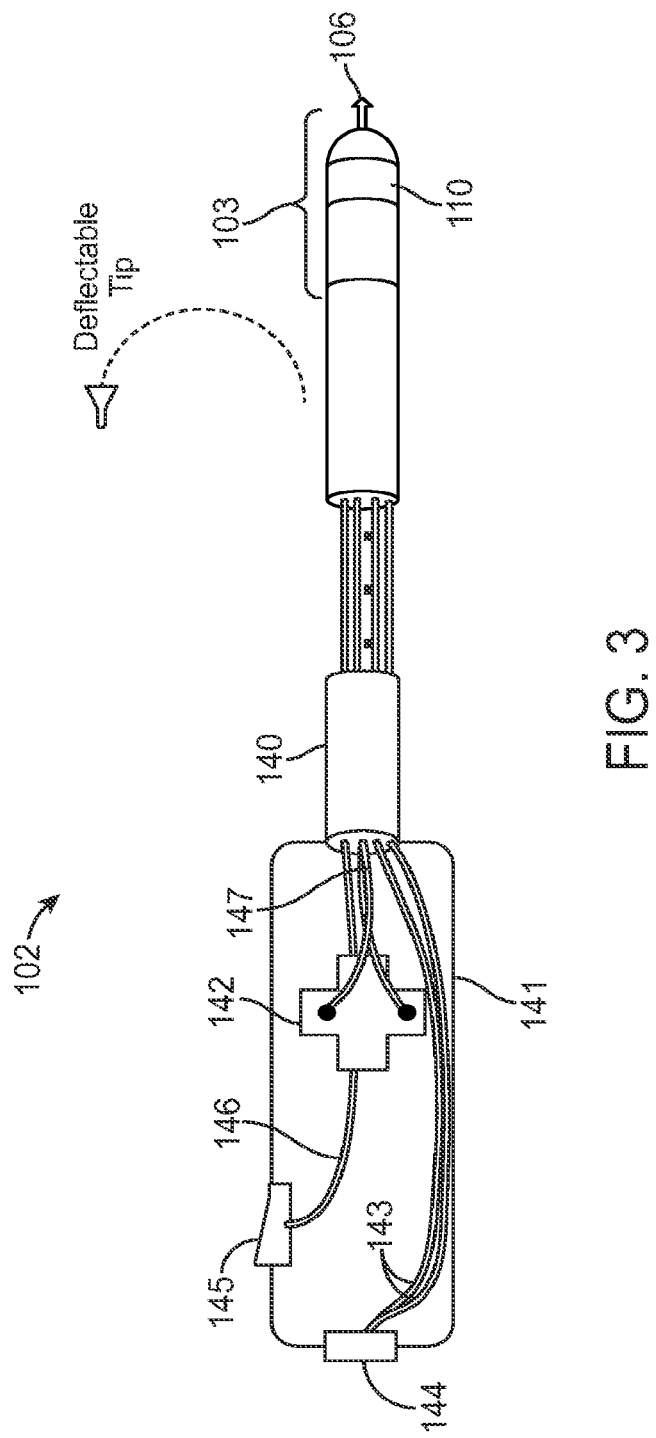
FIG. 3 is a diagrammatic view of a delivery system.

FIG. 3 is a diagrammatic view of a delivery system 102 and its handle 141, in accordance with an embodiment of the present invention.

The delivery system 102 is configured for use in the cardiovascular system of a patient and configured to be compatible with standard transvascular tools, such as introducers and guiding sheaths, and conventional techniques related to the operation of such tools.

The delivery system 102 comprises one or more safety mechanisms, interlocks, or indicators configured to prevent inadvertent attachment or release of the R-S 103.

As mentioned above, the delivery system 102 provides signal interconnect with an external monitor and pacing controller to facilitate location selection during an implant procedure by collecting local EGM signals, performing direct electrical pacing of the heart via electrical connections to one or more of the electrodes of the implantable R-S 103 device, and evaluating operational efficiency of the R-S 103.

In one embodiment, the delivery system shaft 140 is formed from polymer tubing. Conductive wires 143, deflection wires 147 and safety release interlock wires 146 are routed within the shaft 140. A proximal handle assembly 141 comprises a deflection control mechanism 142, a safety interlock release mechanism 145, and shrouded electrical connectors 144 that terminate the conductive wires 143 and permit driving the R-S 103 electrodes directly with an externally-generated electrical pacing pulse, as well as monitoring of cardiac EGM signals at the R-S 103 electrodes.

In one embodiment, the delivery system 102 is configured to attach the R-S in the left ventricle (LV) by prolapsing the shaft 140 in the aortic arch and advancing through the aortic valve of the heart atraumatically, thereby allowing access to targeted endocardial locations within the LV. The distal portion of the delivery system 102 is deflectable in one plane in at least one direction, through the handle-mounted deflection control system. The deflection control system holds a desired deflection angle. Similarly, in other embodiments the delivery system can be configured to attach the R-S in any heart chamber or on the epicardial surface of the heart or within the vasculature of the heart.

The delivery system 102 and/or R-S 103 may comprise one or more radiopaque markers at the distal end to allow fluoroscopic confirmation of the state of R-S 103 deployment. In one embodiment, the markers are configured to clearly differentiate between various stages of deployment, possibly including but not limited to: a) cathode retracted, b) cathode extended, c) attachment tines deployed, d) R-S 103 released, e) tether advanced, f) tether broken, and g) tether retracted.

In one embodiment, the delivery system 102 comprises a control mechanism to extend and retract the needle assembly 115 of the R-S 103. The control mechanism includes a safety mechanism to prevent accidental extension or retraction of the needle assembly 115. The control mechanism and/or the R-S 103 allows for locking the needle assembly 115 into the desired position (retracted or injected as shown in exemplary FIGS. 2a and 2c).

The delivery system 102 comprises a control mechanism to activate the attachment mechanism of the R-S 103, as shown in exemplary FIG. 2d. This control mechanism and/or the R-S 103 design includes an interlock to prevent deployment of the R-S 103 attachment mechanism unless the cathode 106 is extended. The control mechanism to activate the attachment mechanism comprises multiple or multi-stage safety mechanisms to prevent inadvertent activation.

The delivery system 102 also comprises a control mechanism to release the R-S 103, as shown in exemplary FIGS. 2e-2h. The control mechanism and/or the R-S 103 design include an interlock to prevent release of the R-S 103 unless the attachment mechanism has been deployed.

The control mechanism to release the R-S 103 incorporates multiple or multi-stage safety mechanisms to prevent inadvertent activation. The delivery system 102 and/or R-S 103 comprise reliable means to verify a secure implantation prior to permanent release.

The delivery system 102 also comprises a control mechanism to tether out (extend) the R-S 103 away from the main body of the delivery system 102, as shown in exemplary FIG. 2f. The control mechanism and/or the R-S 103 design include an interlock to prevent tethering out of the R-S 103 unless the release mechanism has been deployed. The control mechanism to tether the R-S 103 incorporates multiple or multi-stage safety mechanisms to prevent inadvertent tether extension. The delivery system 102 and/or R-S 103 comprise reliable means to verify a secure implantation prior to detaching the tether. The delivery system 102 and the R-S 103 are removable from the vasculature with the tether extended or with the tether retracted.

The delivery system 102 also comprises a control mechanism to detach the tether and disconnect the temporary electrical connection from the R-S 103, as shown in exemplary FIG. 2g. In one embodiment the control mechanism detaches and disconnects, in alternative embodiments separate mechanisms may be applied to disconnect and detach. The control mechanism and/or the R-S 103 designs include an interlock to prevent disconnecting and detaching the tether of the delivery system 102 unless the release mechanism has been deployed. The control mechanism to disconnect the temporary electrical connection and detach the tether from the R-S 103 incorporates multiple or multi-stage safety mechanisms to prevent inadvertent detachment. The delivery system 102 and/or R-S 103 comprise reliable means to verify a secure implantation prior to disconnecting the temporary electrical connection and detaching the tether. The delivery system 102 is removable from the vasculature with the tether extended or with the tether retracted.

The delivery system 102 is removable from the vasculature by manual withdrawal through an introducer. Any enlargement or protrusion from the delivery system 102 as part of the R-S 103 release mechanism is retractable and/or reversible to allow removal. The delivery system 102 comprises conventional means to protect against accidental release of air into the vasculature or heart chamber before and after release of the R-S 103.

In one embodiment, the delivery system 102 is mated with an R-S 103 prior to packaging. The delivery system 102 and R-S 103 are mated and packaged with the cathode 106 locked in a retracted state. In one embodiment, a delivery system 102 with a pre-mated R-S 103 are packaged in a single-use sterile pouch or tray, and a catheter extension cable is packaged in the same single-use sterile pouch or tray with the delivery system 102 and R-S 103.

Figure 4:
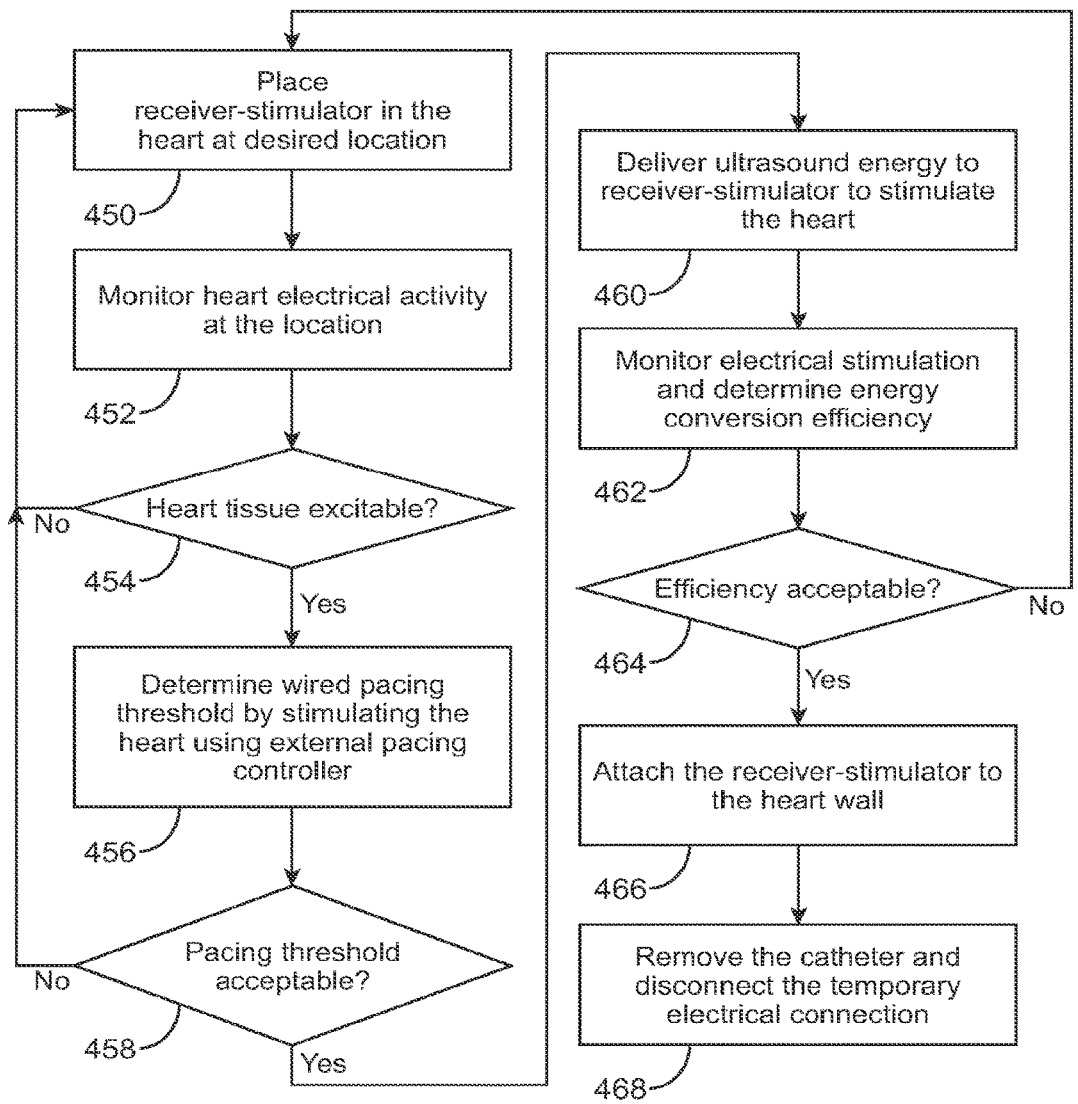
FIG. 4 is a flow diagram illustrating the steps for implantation of a receiver-stimulator into the heart.

FIG. 4 is a flow diagram illustrating a method for implantation of a receiver-stimulator into the heart, in accordance with an embodiment of the present invention. At step 450, an implantable wireless R-S 103 in retracted state is delivered into the heart at a candidate pacing location using a delivery system 102. At step 452 the heart's electrical activity is monitored at the location in the heart as sensed by the cathode 106 in an injected state and an indifferent electrode, possibly anode 110 of the R-S 103. At step 454 it is determined whether the location indicates excitable heart tissue, and if necessary the R-S 103 is repositioned until it is in contact with excitable heart tissue.

Once a location is determined to be excitable, the heart tissue is stimulated at step 456 using electrical stimulation energy from an external pacing controller delivered to the tissue through the cathode 106 in an injected state and an anode, possibly anode 110 of the R-S 103, thereby allowing determination of an acceptable electrical pacing threshold at the location prior to permanent attachment of the R-S 103 to the heart wall. If the pacing threshold is not acceptable, the R-S 103 is repositioned and the above steps are repeated until an acceptable pacing threshold is found.

At step 460, a wireless controller-transmitter (not shown) delivers acoustic energy to the wireless R-S 103, which in turn delivers electrical energy converted by the R-S 103 from the acoustic energy to the heart tissue through the cathode 106 in an injected state and necessarily the anode 110. At the same time, an external monitor, connected at least to the R-S 103 cathode 106 via the temporary electrical connection and to an indifferent electrode, possibly the anode 110 via its temporary electrical connections or alternatively an indifferent electrode 110C on the delivery system 102 or the indifferent electrode 110P, monitors and quantifies the delivered electrical energy at step 462 to determine the efficiency of conversion of acoustic energy to electrical energy by the R-S 103 at the current location and position in the heart.

As can be understood, electromagnetic energy (e.g., RF), could also be delivered wirelessly to the receiver-stimulator and the rest of the features and functionalities of the delivery system disclosed here could be used to identify the optimal location for the implant to efficiently stimulate heart tissue.

In one embodiment, the delivered electrical energy is at pacing strength to stimulate the tissue and the EGM generated by the stimulation of heart tissue is monitored using the temporary electrical connections to the cathode 106 and anode 110 to determine acoustic to electrical conversion efficiency. In an alternative embodiment, the delivered electrical energy is not at pacing/stimulation strength, but instead is at a level below the stimulation threshold; hence conversion efficiency can be gauged even at lower energy levels. In such an alternative embodiment, electrical monitoring via the temporary electrical connections to the cathode 106 and an anode, possibly the anode 110 via its temporary electrical connections or alternatively an indifferent electrode 110C on the delivery system 102 or indifferent electrode 110P that is remote from the delivery system, indicates the level of electrical energy generated by the R-S 103. A comparison of this level of generated electrical energy against the amount of acoustic energy transmitted to the R-S 103 indicates the conversion efficiency of the R-S 103.

When a suitable implantation location is determined, at step 466 the R-S 103 is attached to the heart wall in the triggered state, and at step 468 the temporary electrical connections to the cathode 106 and anode 110 are disconnected using a disconnect mechanism as the R-S 103 goes through the sequence of released state, tethered state, tether broken state, and delivered state, as described above in FIGS. 2e-2h.

While the above exemplary embodiments of the R-S 103 shown in FIGS. 2a-g use a particular disconnect mechanism for the temporary electrical connection to the cathode 106, comprising a sealed enclosure 117 around a breakable neck 119 segment of the needle assembly 115, there are a variety of other disconnect mechanisms for the cathode 106 temporary electrical connection that are contemplated herein. We now turn to describing such further embodiments.

Figure 5A:
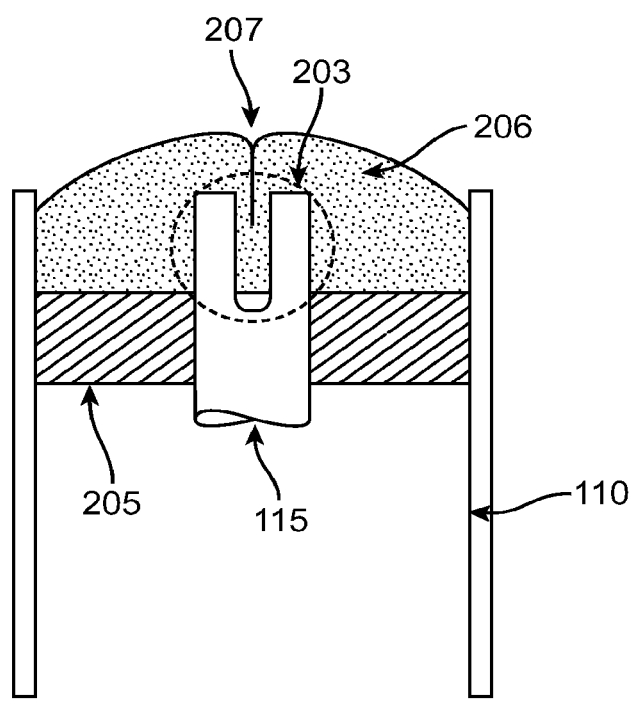
FIG. 5a is a diagrammatic view of a sealed disconnect mechanism of a wireless receiver-stimulator.

FIG. 5a is a diagrammatic view of a sealed disconnect mechanism 108 of a wireless R-S 103, in accordance with an embodiment of the present invention, providing a temporary electrical connection between an electrical contact at a proximal position of the R-S 103 and an electrical contact at a distal position of the catheter assembly 102. In this embodiment, the proximal end of the wireless R-S 103 comprises a connector receptacle 203 as part of a needle assembly 115. The proximal tip of the connector receptacle 203 represents the electrical contact at a proximal position of the R-S 103. The needle assembly 115 is insulated from the anode 110 by an insulator 205. The insulator 205 may comprise ceramic, glass, or other insulating material, and additionally creates a hermetic seal between the body of the R-S 103 and the connector 203.

Figure 5B:
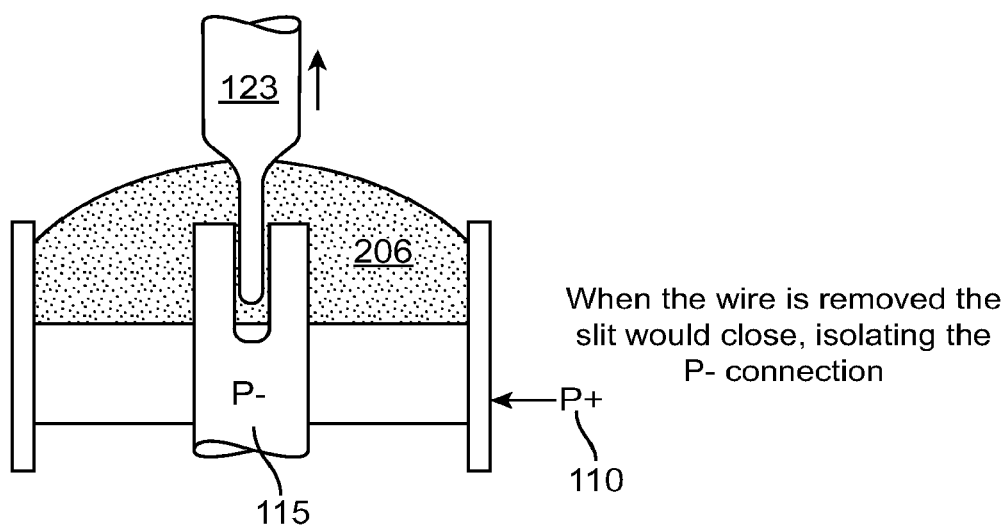
FIG. 5b is a diagrammatic view of a conductive wire passing through a hole or slit of the sealed disconnect mechanism of FIG. 2a and connecting with the cathode.

The connector receptacle 203 is at the proximal end of the needle assembly 115 and is electrically connected to the cathode 106 via the needle assembly 115. A seal 206 covers the connector receptacle 203 and comprises a hole or slit 207 to allow the conductive wire 123 of the delivery system 102 to pass through and electrically connect to the cathode 106 (via the connection to the connector receptacle 203). The distal tip of the conductive wire 123 represents the electrical contact at a distal position of the catheter assembly 102. This is shown in FIG. 5b. The seal 206 may comprise silicone, rubber or other flexible insulating material.

In one embodiment, the seal 206 is compressed so that the hole or slit 207 is forced closed when the wire 123 is withdrawn, thereby isolating the connector receptacle 203 and the needle assembly 115 from patient fluid or tissue. The seal 206 need not necessarily be hermetic, but it is configured to provide high enough electrical resistance through the temporary electrical path to the connector receptacle 203 to allow substantially any electrical current to flow through the electrical path of the cathode 106 to the anode 110.

Figure 5C:
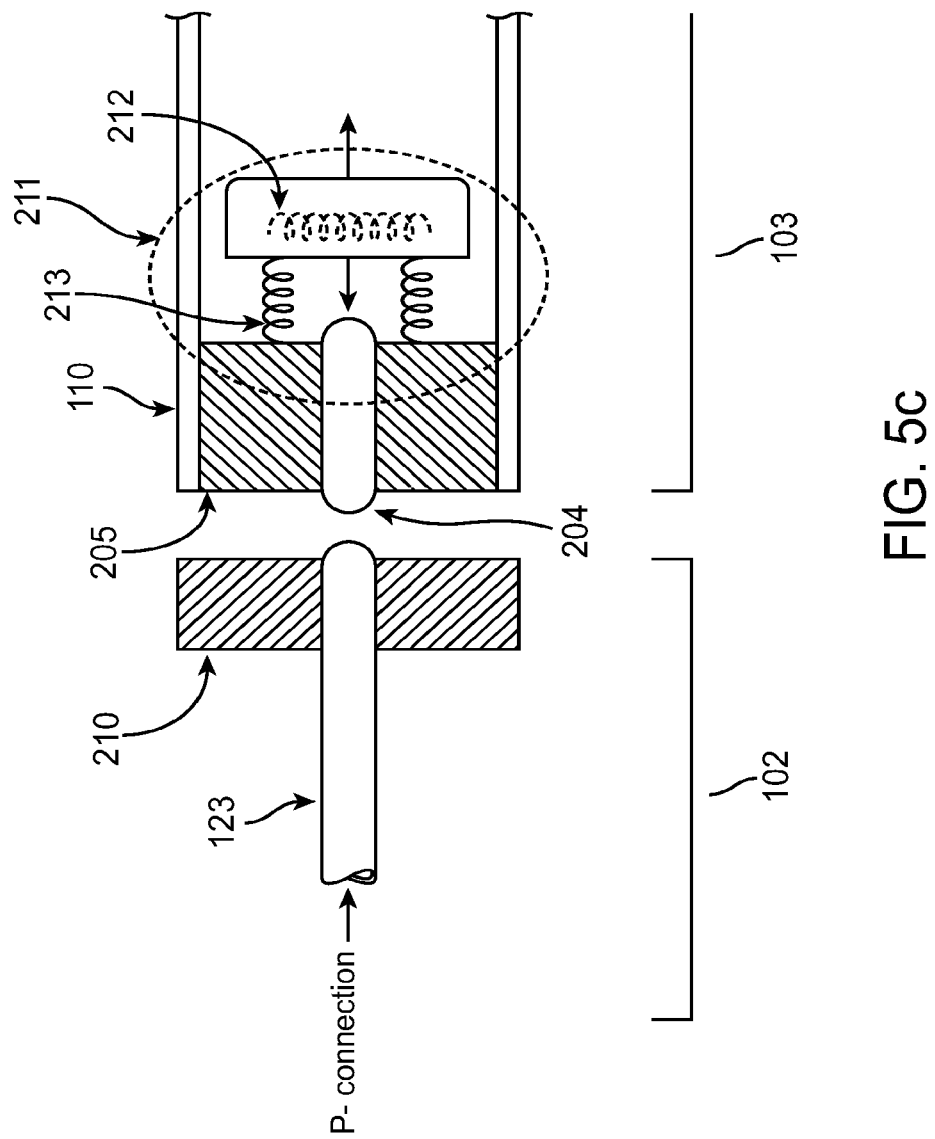
FIG. 5c is a diagrammatic view of a magnetically operated disconnect mechanism.

Instead of a seal, a magnetically operated switch internal to the wireless R-S 103 can be used to electrically connect the wire 123 to the cathode 106. FIG. 5c is a diagrammatic view of a magnetically operated disconnect mechanism, in accordance with a first such embodiment of the present invention. This embodiment comprises a magnetically operated switch 211 internal to the R-S 103. The delivery system 102 comprises a magnet 210 at its distal tip, and a magnetic metal disk 212 is attracted to the feed-through 204 by the catheter magnet 210. The magnet 210 on the distal end of the delivery system 102 holds the switch 211 closed when the wireless R-S 103 is attached to the delivery system 102, bringing the magnetic metal disk 212, which is in contact with the cathode 106, into contact with a feed-through 204.

One or more springs 213 push the disk 212 away and hold the switch 211 open when the catheter magnet 210 detaches from R-S 103 and is withdrawn, at which point the switch 211 opens and the temporary electrical connection from the cathode 106 to the feed-through 204 is disconnected. FIG. 5c shows the delivery system 102 removed and the switch 211 open.

Figure 5D:
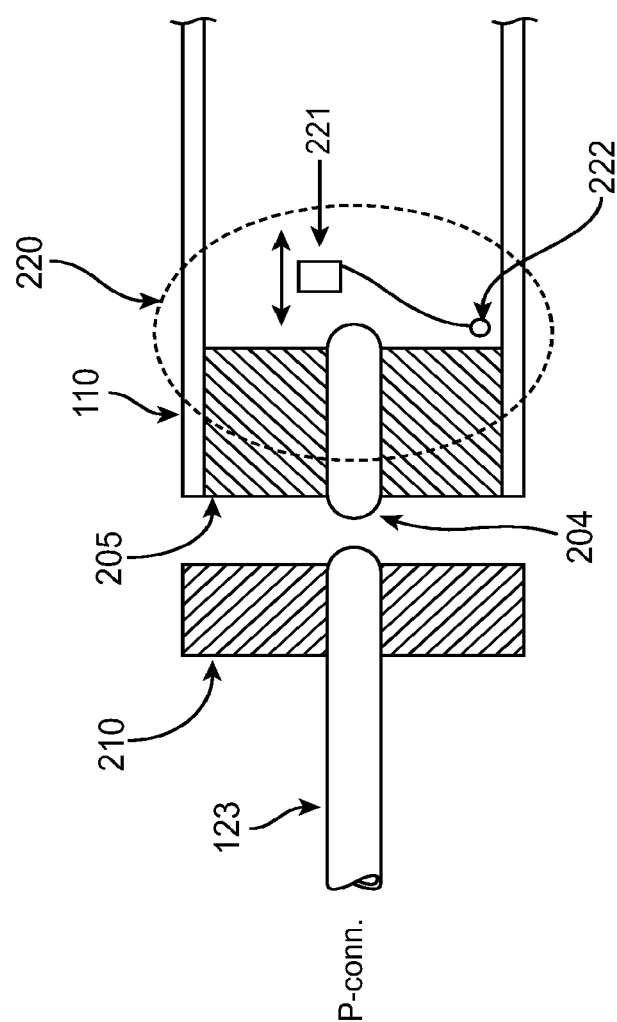
FIG. 5d is a diagrammatic view of a magnetically operated disconnect mechanism.

FIG. 5d is a diagrammatic view of a magnetically operated disconnect mechanism, in accordance with a second such embodiment of the present invention. In this embodiment, the magnetically operated switch 220 is a "reed" switch. The reed switch 220 comprises a magnet 221 on the end of the reed lever 222. Alternately, the reed lever 222 could be made of a magnetic metal, eliminating the need for magnet 221. The magnet 221 is attracted to the feed-through 204 by a catheter magnet 210 and closes the switch 220 when the delivery system 102 is attached to the wireless R-S 103. The reed switch 220 springs back when the catheter magnet 210 is detached from R-S 103 and is withdrawn, thereby causing electrical disconnection.

Figure 5E:
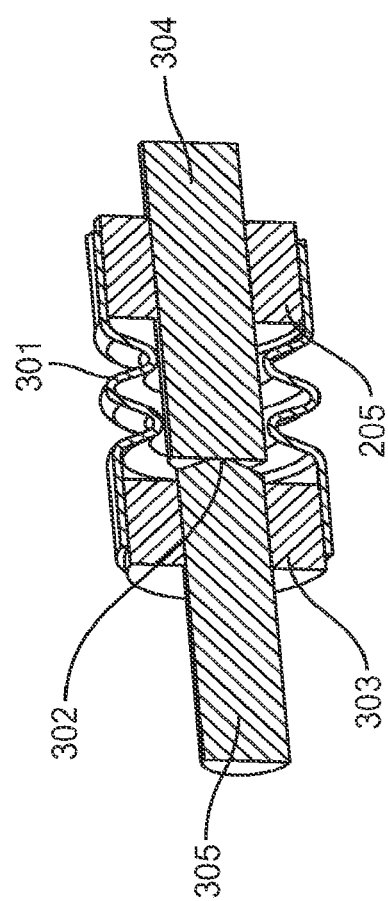
FIGS. 5e-f are diagrammatic views of a disconnect mechanism using a bellows.
Figure 5F:
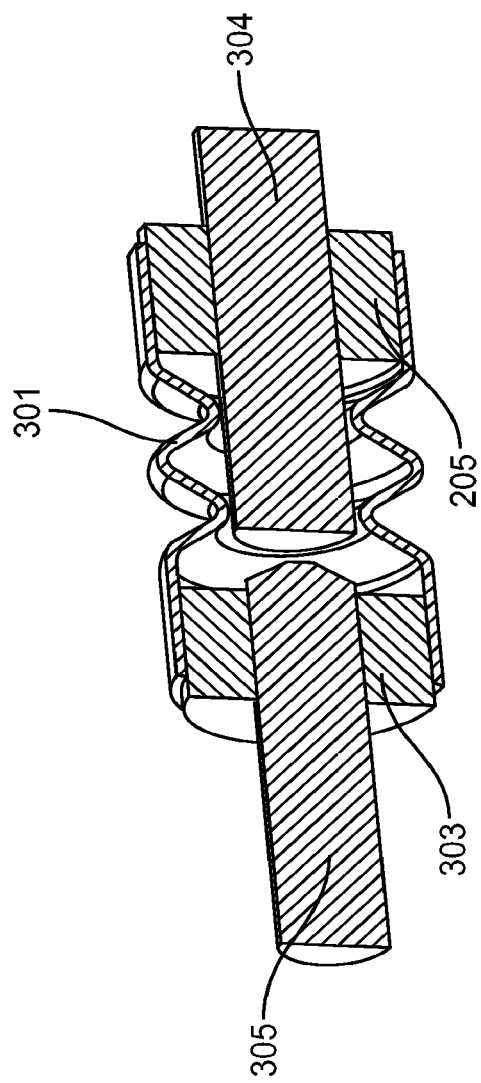

FIGS. 5e-f are diagrammatic views of a disconnect mechanism using bellows, in accordance with an embodiment of the present invention. The disconnect mechanism comprises bellows 301 comprising an inside lead 304 on the distal end of the bellows 301 and an outside lead 305 on the proximal end of the bellows 301. The inside lead 304 is electrically connected to the cathode 106 via the needle assembly. The outside lead 305 may comprise a proximal segment for connecting with the conductive wire 123 of the catheter via a connecting collar, similar to the embodiment described in FIGS. 2a-g, and a mechanism for mechanical disconnection. The proximal segment, needle assembly, and connecting collar are not shown in FIGS. 5e-f, but they are analogous to those described above with reference to FIGS. 2a-g.

The bellows 301 is initially configured such that the outside lead 305 is in electrical contact with the inside lead 304 at the electrical contact point 302 as shown in FIG. 5e, thereby providing a temporary electrical connection between the conductive wire 123 of the delivery system 102 and the cathode 106. The bellows 301 stretches when the delivery system 102 is retracted and pulled away from the wireless R-S 103, thereby disconnecting the temporary electrical connection to the cathode 106, as shown in FIG. 5f. When the delivery system 102 is retracted, it also detaches the delivery system 102 from the R-S 103. Note that while this leaves the outside lead 305 physically connected to the bellows 301 and hence to the R-S 103, the outside lead 305 is electrically isolated from the cathode 106. In one embodiment, the insulator 205 is hermetically connected to the enclosure of the wireless R-S 103.

Figure 5G:
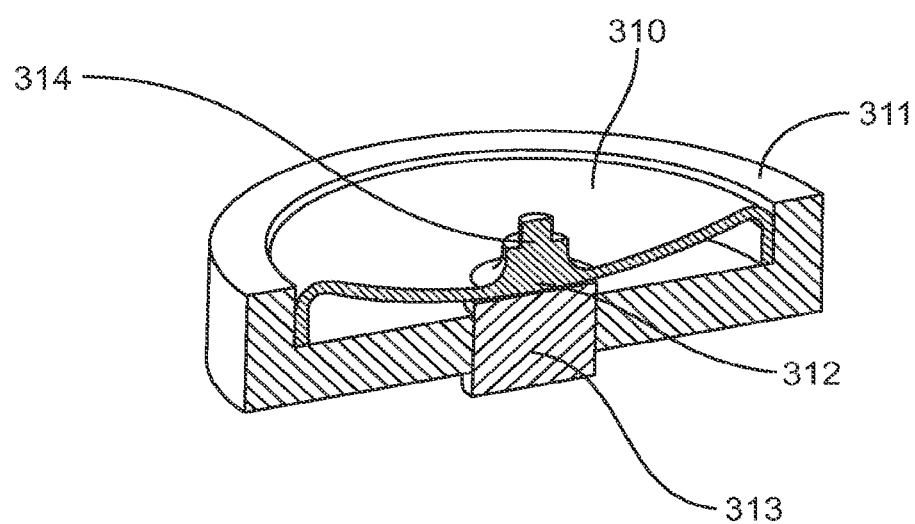
FIGS. 5g-h are diagrammatic views of a disconnect mechanism using a conductive dome structure.
Figure 5H:
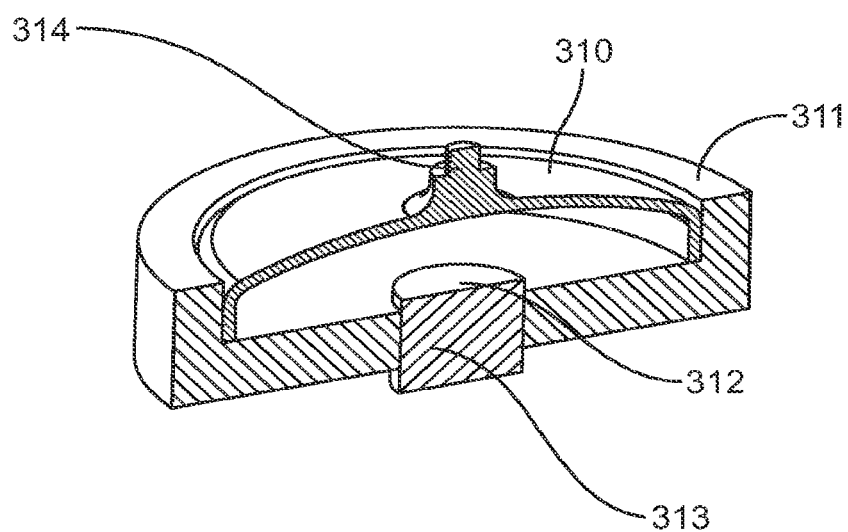

FIGS. 5g-h are diagrammatic views of a disconnect mechanism using a conductive dome structure, in accordance with an embodiment of the present invention. The disconnect mechanism comprises an inside lead 313 on the distal end of the disconnect mechanism and a conductive dome structure 310 with a feature 314 on the proximal end of the disconnect mechanism. The inside lead 313 is electrically connected to the cathode 106 via the needle assembly. The conductive dome structure 310 is housed within an insulating cup 311. The insulating cup 311 comprises ceramic or other insulating material. The feature 314 may comprise a proximal segment for connecting with the conductive wire 123 of the catheter via a detachable connecting collar, similar to the embodiment described in FIGS. 2a-g.

The proximal segment, needle assembly, and connecting collar are not shown in FIGS. 5e-f, but they are analogous to those described above with reference to FIGS. 2a-g.

The conductive dome structure 310 is initially configured such that it is in electrical contact with the inside lead 313 at the electrical contact point 312 as shown in FIG. 5g, thereby providing an electrical path between the conductive wire 123 of the delivery system 102 and the cathode 106. The conductive dome structure 310 pops out when the delivery system 102 is retracted and pulled away from the wireless R-S 103, thereby disconnecting the temporary electrical connection to the cathode 106, as shown in FIG. 5h. When the delivery system 102 is retracted, it detaches the delivery system 102 from the R-S 103. Note that while this leaves the conductive dome structure 310 physically connected to the R-S 103, the conductive dome structure 310 is electrically isolated from the cathode 106. In one embodiment, the insulating cup 311 is hermetically connected to the enclosure of the wireless R-S 103, the inside lead 313, and the conductive dome structure 310, as shown in FIG. 5h.

In an alternative embodiment, the disconnect mechanism comprises a fuse internal to the R-S 103. Once a suitable implant location has been determined and the R-S 103 has been attached to the heart, the fuse is opened (blown) by delivering sufficient current through the conductive wire 123 of the delivery system 102. The opened fuse disconnects the temporary electrical connection to the cathode 106. Alternatively, the disconnect mechanism may comprise an electronic switch internal to the R-S 103 which when activated disconnects the temporary electrical connection to the cathode 106.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

What is claimed is:

1. A device, comprising:
   a receiver-stimulator implantable in the heart of a patient using a delivery system and configured to receive controlled acoustic energy from a controller-transmitter and to convert the acoustic energy to electrical energy, the receiver-stimulator comprising:
   at least two electrodes configured to deliver electrical energy;
   one or more temporary electrical connection(s) between the electrode(s) and the delivery system; and
   a disconnect mechanism to disconnect the temporary electrical connection;
   wherein the temporary electrical connection(s) is configured to be connected to an external monitor to determine an efficiency of conversion of acoustic energy to electrical stimulation energy at the location by comparing a level of the delivered electrical energy against the acoustic energy transmitted by the controller-transmitter.

2. The device of claim 1, wherein the delivery system is a catheter-based assembly.

3. The device of claim 1 configured to stimulate the heart using the two electrodes, wherein the two electrodes are an anode and a cathode, and wherein the temporary electrical connection is between the cathode and the delivery system.

4. The device of claim 1 configured to stimulate the heart using the two electrodes, wherein the two electrodes are an anode and a cathode, and wherein the temporary electrical connection is between the anode and the delivery system.

5. The device of claim 1 configured to stimulate the heart using the two electrodes, wherein the two electrodes are an anode and a cathode, and wherein the temporary electrical connections are a first temporary electrical connection between the cathode and the delivery system and a second temporary electrical connection between the anode and the delivery system.

6. The device of claim 5, wherein the first temporary electrical connection is between a first electrical contact at a first proximal position of the receiver-stimulator and a first electrical contact at a first distal position of the delivery system assembly, and wherein the disconnect mechanism is further configured to insulate the first electrical contact at the first proximal position of the receiver-stimulator from a conductive path to the patient.

7. The device of claim 6, wherein the disconnect mechanism comprises a connector receptacle allowing a conductive wire to feed through from the delivery system assembly to the first electrical contact at the first proximal position of the receiver-stimulator, and wherein the connector receptacle is covered by a compressed seal configured to close when the conductive wire is withdrawn.

8. The device of claim 7, wherein the seal comprises silicone or rubber.

9. The device of claim 6, wherein the disconnect mechanism is further configured to electrically isolate the first electrical contact at the first proximal position of the receiver-stimulator from the cathode.

10. The device of claim 9, wherein the disconnect mechanism comprises a magnetically operated switch in the receiver-stimulator.

11. The device of claim 10, wherein the magnetically operated switch is held closed by a magnet on the distal end of the delivery system assembly, and wherein the switch is opened by one or more springs upon detaching the delivery system and disconnects the first temporary electrical connection.

12. The device of claim 10, wherein the magnetically operated switch is a reed switch held closed by a magnet on the distal end of the delivery system assembly, and wherein the reed switch opens upon detaching the delivery system and disconnects the first temporary electrical connection.

13. The device of claim 9, wherein the disconnect mechanism comprises a bellows that stretches when the delivery system is detached from the receiver-stimulator, thereby disconnecting the first temporary electrical connection.

14. The device of claim 13, wherein the bellows is held compressed while connected to the delivery system and springs open when released from the delivery system.

15. The device of claim 9, wherein the disconnect mechanism comprises a conductive dome structure that bulges outward when the delivery system is detached from the receiver-stimulator, thereby disconnecting the first temporary electrical connection.

16. The device of claim 1, wherein the disconnect mechanism comprises a fuse that is opened to disconnect the temporary electrical connection.

17. The device of claim 1, wherein the disconnect mechanism comprises an electronic switch which when activated disconnects the temporary electrical connection.

18. A catheter-based delivery system for implantation of a receiver-stimulator into the heart of a patient, comprising:
- a catheter assembly having a proximal end and a distal end, the catheter assembly comprising:
- a receiver-stimulator detachably attached at the distal end of the catheter assembly, the receiver-stimulator configured to convert received acoustic energy from a controller-transmitter to electrical energy, wherein said receiver-stimulator comprises a cathode and an anode, both configured to be in electrical contact with the patient for stimulating the heart;
- a first temporary electrical connection between the cathode and the catheter assembly, the electrical connection extending through the catheter assembly;
- a disconnect mechanism to disconnect the first temporary electrical connection; and an indifferent electrode, the indifferent electrode in electrical contact with the patient;
- wherein the cathode and the indifferent electrode are configured to monitor heart electrical activity and to stimulate the heart to determine an efficiency of conversion of acoustic energy to electrical stimulation energy at the location that is determined to be excitable by comparing a level of the delivered electrical energy against the acoustic energy transmitted by the controller-transmitter.

19. The catheter-based delivery system of claim 18, wherein the system further comprises a second temporary electrical connection between the anode and the catheter assembly and the electrical connection extending through the catheter assembly, and further comprises a disconnect mechanism to disconnect the second temporary electrical connection wherein the cathode and the anode are configured to monitor heart electrical activity and to stimulate the heart.

20. The catheter-based delivery system of claim 18, wherein the indifferent electrode is disposed on the catheter assembly with an electrical connection extending through the catheter assembly.

21. The catheter-based delivery system of claim 18, wherein the indifferent electrode is remote from the delivery system.

22. A method for determining the efficiency of operation of a wireless tissue stimulation system, comprising:
- transmitting energy from a controller-transmitter towards an implantable receiver-stimulator comprising a cathode stimulation electrode and an anode stimulation electrode, wherein the receiver-stimulator is configured to be mounted on a catheter assembly, and wherein the catheter assembly is configured to implant the receiver-stimulator; and
- measuring electrical energy converted by the receiver-stimulator from the transmitted energy; wherein the measuring comprises analyzing an electrogram between two temporary electrical connections connected to the two stimulation electrodes of the receiver stimulator; determining an efficiency of conversion of acoustic energy to electrical stimulation energy at the location that is determined to be excitable by comparing a level of the delivered electrical energy against the acoustic energy transmitted by the controller-transmitter and correlating the efficiency of conversion with the likelihood of pacing of the heart issue.

23. A method for determining the efficiency of operation of a wireless tissue stimulation system, comprising:
- transmitting energy from a controller-transmitter towards an implantable receiver stimulator comprising a cathode stimulation electrode and an anode stimulation electrode, wherein the receiver-stimulator is configured to be mounted on a catheter assembly, and wherein the catheter assembly is configured to implant the receiver-stimulator; and
- measuring electrical energy converted by the receiver-stimulator from the transmitted energy; wherein the measuring comprises analyzing an electrogram between a temporary electrical connection connected to at least one of the two stimulation electrodes of the receiver stimulator and an indifferent electrode; determining an efficiency of conversion of acoustic energy to electrical stimulation energy at the location that is determined to be excitable by comparing a level of the delivered electrical energy against the acoustic energy transmitted by the controller-transmitter and correlating the efficiency of conversion with the likelihood of pacing of the heart issue.

24. The method of claim 23, wherein the indifferent electrode is mounted on the catheter assembly.

25. The method of claim 23, wherein the indifferent electrode is remote from the catheter assembly.

* * * * *